US009447018B2

(12) United States Patent
Gadewar et al.

(10) Patent No.: US 9,447,018 B2
(45) Date of Patent: Sep. 20, 2016

(54) ETHYL ACETATE PRODUCTION

(71) Applicant: Greenyug, LLC, Santa Barbara, CA (US)

(72) Inventors: Sagar B. Gadewar, Goleta, CA (US); Peter K. Stoimenov, Goleta, CA (US)

(73) Assignee: Greenyug, LLC, Santa Barbara, CA (US)

( * ) Notice: Subject to any disclaimer, the term of this patent is extended or adjusted under 35 U.S.C. 154(b) by 209 days.

(21) Appl. No.: 14/023,125

(22) Filed: Sep. 10, 2013

(65) Prior Publication Data

US 2014/0012037 A1  Jan. 9, 2014

Related U.S. Application Data

(63) Continuation-in-part of application No. 12/925,460, filed on Oct. 20, 2010, now Pat. No. 8,558,025.

(60) Provisional application No. 61/253,349, filed on Oct. 20, 2009.

(51) Int. Cl.
| | | |
|---|---|---|
| C07C 67/40 | (2006.01) | |
| C07C 67/48 | (2006.01) | |
| B01D 3/40 | (2006.01) | |
| C07C 67/58 | (2006.01) | |
| B01D 3/00 | (2006.01) | |

(52) U.S. Cl.
CPC .............. *C07C 67/58* (2013.01); *B01D 3/001* (2013.01); *B01D 3/009* (2013.01); *C07C 67/40* (2013.01); *Y02P 20/127* (2015.11); *Y02P 20/582* (2015.11)

(58) Field of Classification Search
CPC ....... C07C 67/58; C07C 67/40; C07C 69/14; B01D 3/009
See application file for complete search history.

(56) References Cited

U.S. PATENT DOCUMENTS

| | | | |
|---|---|---|---|
| 1,992,480 A | 2/1935 | Fuchs et al. | |
| 2,525,829 A | 10/1950 | Royer et al. | |
| 2,544,562 A * | 3/1951 | Vesta | C07C 45/85 518/727 |
| 3,714,236 A | 1/1973 | Wright, Jr. et al. | |
| 4,052,424 A | 10/1977 | Vanderspurt | |
| 4,220,803 A | 9/1980 | Marcinkowsky et al. | |
| 4,379,028 A * | 4/1983 | Berg | B01D 3/40 203/51 |
| 4,435,595 A | 3/1984 | Agreda et al. | |
| 4,440,946 A | 4/1984 | Summerville et al. | |
| 4,523,027 A | 6/1985 | Kummer et al. | |
| 4,569,726 A | 2/1986 | Berg et al. | |
| 4,645,570 A | 2/1987 | Sridhar et al. | |
| 4,825,013 A | 4/1989 | Quarderer et al. | |
| 4,996,007 A | 2/1991 | Chao et al. | |
| 5,194,675 A | 3/1993 | Joerg et al. | |
| 5,334,751 A | 8/1994 | Lemanski et al. | |
| 6,407,295 B1 | 6/2002 | Kaizik et al. | |
| 6,632,330 B1 * | 10/2003 | Colley | C07C 67/54 203/18 |
| 6,809,217 B1 | 10/2004 | Colley et al. | |
| 7,700,810 B2 | 4/2010 | Kourtakis et al. | |
| 7,700,811 B2 | 4/2010 | Kourtakis et al. | |
| 7,700,812 B2 | 4/2010 | Kourtakis et al. | |
| 7,700,813 B2 | 4/2010 | Kourtakis et al. | |
| 7,705,192 B2 | 4/2010 | Kourtakis et al. | |
| 7,745,672 B2 | 6/2010 | Kourtakis et al. | |
| 8,071,823 B2 | 12/2011 | Ozer et al. | |
| 8,080,684 B2 | 12/2011 | Hassan et al. | |
| 8,080,695 B2 | 12/2011 | Tsuchida et al. | |
| 8,304,587 B2 | 11/2012 | Warner et al. | |
| 8,318,989 B2 | 11/2012 | Kourtakis et al. | |
| 8,558,025 B2 | 10/2013 | Gadewar | |
| 8,562,921 B2 | 10/2013 | Gadewar | |
| 9,018,427 B2 | 4/2015 | Gadewar et al. | |
| 2006/0178524 A1 | 8/2006 | Zuber et al. | |
| 2013/0197266 A1 | 8/2013 | Gadewar et al. | |

FOREIGN PATENT DOCUMENTS

| | | |
|---|---|---|
| BR | 9104652 A | 4/1993 |
| EP | 0101910 A1 | 3/1984 |
| EP | 0151886 A1 | 8/1985 |
| EP | 0201105 A1 | 11/1986 |
| EP | 0331021 A1 | 9/1989 |
| FR | 2743060 A1 | 7/1997 |
| GB | 287846 | 4/1929 |
| GB | 312345 | 8/1930 |
| GB | 470773 | 8/1937 |

(Continued)

OTHER PUBLICATIONS

Tsai et al, Industrial and Engineering Chemistry Research, Design and Control of the Side Reactor Configuration for Production of Ethyl Acetate, 2008, 47, pp. 9472-9484.*
Stevens et al, Kirk-Othmer Encyclopedia of Chemical Technology, Extraction, Liquid-Liquid, 2007, pp. 1-62.*
Foreign communication from a related counterpart application—International Preliminary Report on Patentability, PCT/US2013/024104, Aug. 5, 2014, 9 pages.
Foreign communication from a related counterpart application—International Search Report and Written Opinion, PCT/US2014/053894, Oct. 31, 2014, 9 pages.
Office Action dated Oct. 27, 2014 (17 pages), U.S. Appl. No. 14/183,273, filed Feb. 18, 2014.

(Continued)

*Primary Examiner* — Paul A Zucker
(74) *Attorney, Agent, or Firm* — Andrew M. Metrailer; Conley Rose, P.C.

(57) ABSTRACT

A method of purifying an ethyl acetate stream comprises contacting an inlet stream with a solvent, transferring at least a portion of the impurity compound from the inlet stream into the solvent to form an extract and a purified product, separating the extract from the purified product, separating the portion of the impurity compound from the extract, forming an impurities stream and a regenerated solvent, and recycling at least a portion of the regenerated solvent to contact the inlet stream. The inlet stream comprises ethyl acetate and an impurity compound, and the extract comprises the solvent and the portion of the impurity compound transferred from the inlet stream.

26 Claims, 17 Drawing Sheets

(56) References Cited

FOREIGN PATENT DOCUMENTS

| JP | 59025334 A | 2/1984 |
|---|---|---|
| JP | 5186392 A | 7/1993 |
| JP | 7053676 B2 | 6/1995 |
| SU | 362814 A1 | 12/1972 |
| WO | 2011131609 A2 | 10/2011 |
| WO | 2013055334 A1 | 4/2013 |
| WO | 2013116492 A1 | 8/2013 |

OTHER PUBLICATIONS

Inui, Kanichiro, et al., "Effective formation of ethyl acetate from ethanol over Cu—Zn—Zr—Al—O catalyst," Journal of Molecular Catalysis A: Chemical, 2004, pp. 147-156, vol. 216, Elsevier B.V.

Inui, Kanichiro, et al., "Direct synthesis of ethyl acetate from ethanol carried out under pressure," Journal of Catalysis, 2002, pp. 207-215, vol. 212, Elsevier Science.

Santacesaria, E., et al., "Ethanol dehydrogenation to ethyl acetate by using copper and copper chromite catalysts," Chemical Engineering Journal, 2012, pp. 209-220, vol. 179, Elsevier B.V.

Takeshita, Kenji, et al., "Reduced copper catalyzed conversion of primary alcohols into esters and ketones," Bulletin of the Chemical Society of Japan, Sep. 1978, pp. 2622-2627, vol. 51, No. 9.

Tsai, Reui-Chiang, et al., "Design and control of the side reactor configuration for production of ethyl acetate," Ind. Eng. Chem. Res., 2008, pp. 9472-9484, vol. 47, No. 23, American Chemical Society.

Filing receipt and specification for provisional patent application entitled "Ethyl acetate production," by Sagar B. Gadewar, filed Oct. 20, 2009 as U.S. Appl. No. 61/253,349.

Foreign communication from a related counterpart application—International Search Report and Written Opinion, PCT/US2011/056015, May 24, 2012, 8 pages.

Foreign communication from a related counterpart application—International Search Report and Written Opinion, PCT/US2013/024104, May 30, 2013, 12 pages.

Machine translation (9 pages) of French patent No. 2743060 A1 issued on Jul. 4, 1997.

Smith, Michael B., "March's advanced organic chemistry: reactions, mechanisms, and structure," 7th edition, 2013, 8 pages of cover, publishing information, and contents, John Wiley & Sons, Inc.

Vogel, Arthur Israel, "Vogel's textbook of practical organic chemistry," 5th edition, revised by Brian S. Furniss, et al., 1989, 15 pages of cover, publishing information, and contents, John Wiley & Sons, Inc.

Foreign communication from a related counterpart application—International Search Report and Written Opinion, PCT/US2014/016957, Jun. 27, 2014, 9 pages.

Notice of Allowance dated Mar. 11, 2015 (30 pages), U.S. Appl. No. 13/363,858, filed Feb. 1, 2012.

Notice of Allowance dated Jan. 6, 2015 (12 pages), U.S. Appl. No. 14/183,273, filed Feb. 18, 2014.

Filing receipt and specification for patent application entitled "Production of higher alcohols," by Sagar B. Gadewar, et al., filed Feb. 18, 2014 as U.S. Appl. No. 14/183,273.

Filing receipt and specification for provisional patent application entitled "Production of butanols and ethyl acetate," by Sagar B. Gadewar, et al., filed Feb. 19, 2013 as U.S. Appl. No. 61/766,484.

Filing receipt and specification for provisional patent application entitled "Production of higher alcohols from ethanol," by Brian Christopher Vicente, et al., filed Dec. 5, 2013 as U.S. Appl. No. 61/912,235.

Yang, Ke Wu, et al., "One-step Synthesis of n-Butanol from Ethanol Condensation over Alumina-supported Metal Catalysts," Chinese Chemical Letters, 2004, pp. 1497-1500, vol. 15, No. 12.

Filing receipt and specification for provisional patent application entitled "Production of ethyl acetate and butyl acetates from ethanol," by Sagar B. Gadewar, et al., filed Dec. 4, 2013 as U.S. Appl. No. 61/911,832.

Filing receipt and specification for international application entitled "Production of higher alcohols," filed Feb. 18, 2014 as international application No. PCT/US2014/016957.

Filing receipt and specification for international application entitled "Ethyl acetate production," filed Oct. 20, 2010 as international application No. PCT/US2010/002806.

Foreign communication from a related counterpart application—International Preliminary Report on Patentability, PCT/US2011/056015, Apr. 15, 2014, 6 pages.

Foreign communication from a related counterpart application—Search Report, European Application No. 11873809.5 filed on Apr. 15, 2015.

\* cited by examiner

Figure 1: Reactive residue curve maps at pressures of 1 atm and 5 atm.

Figure 2: Reactive residue curve maps at pressures of 10 atm and 20 atm.

Figure 3: Single feed reactive distillation column schematic.

Figure 4: Schematic for a reactive distillation system with subsequent product hydrogenation.

Figure 5: Double feed reactive distillation column schematic with an upper feed of ethanol and lower feed of hydrogen.

Figure 6: Double feed reactive distillation column schematic using dual catalyst beds with an upper feed of ethanol and lower feed of hydrogen.

Figure 7: Side reactor configuration (a) upward flow feed to side reactor (b) downward flow feed to side reactor.

Figure 8: Double Side reactor configuration (a) upward flow feed to multiple side reactors (b) downward flow feed to multiple side reactors.

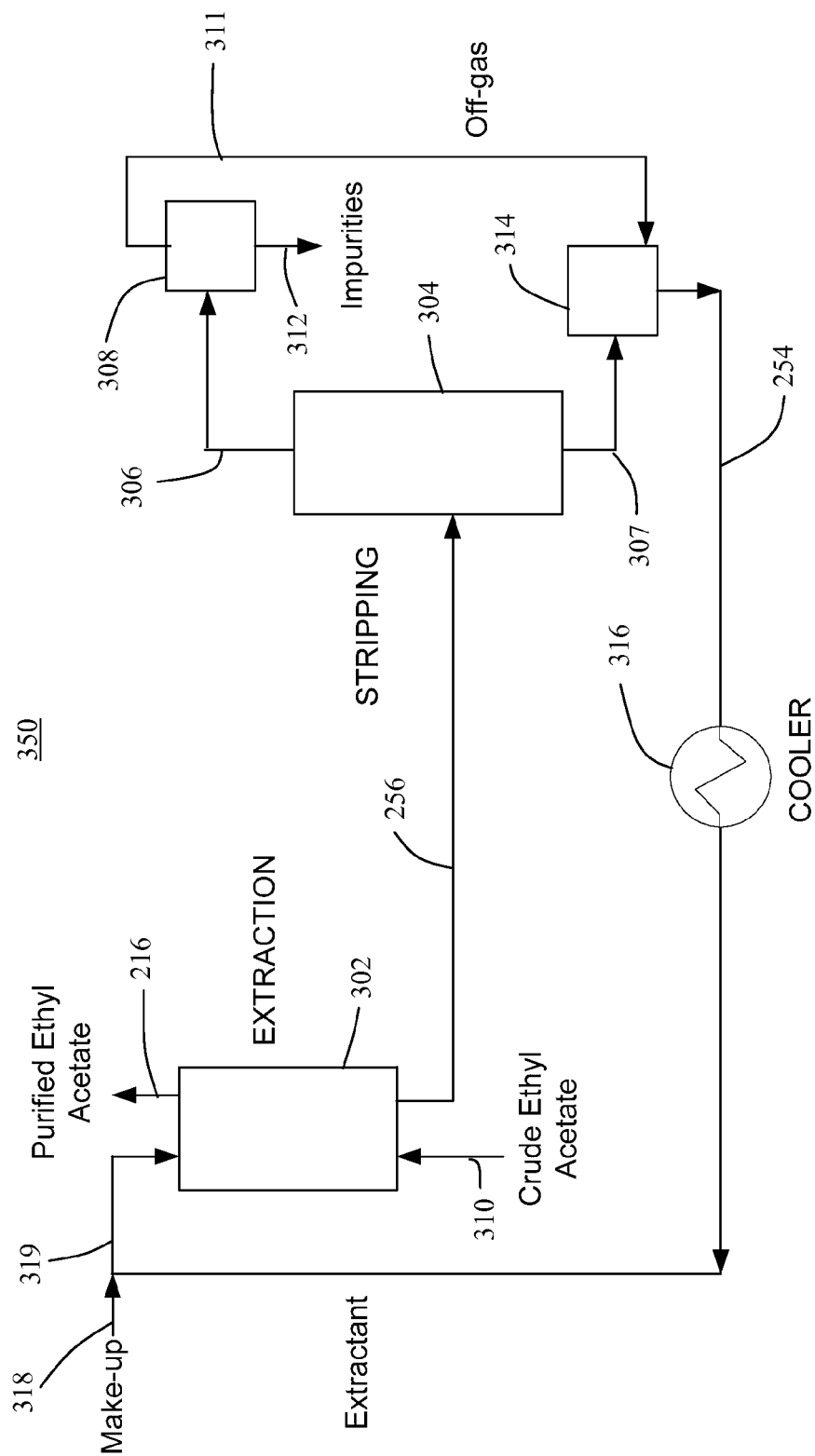
Figure 11. Schematic for Extraction-Stripping Process

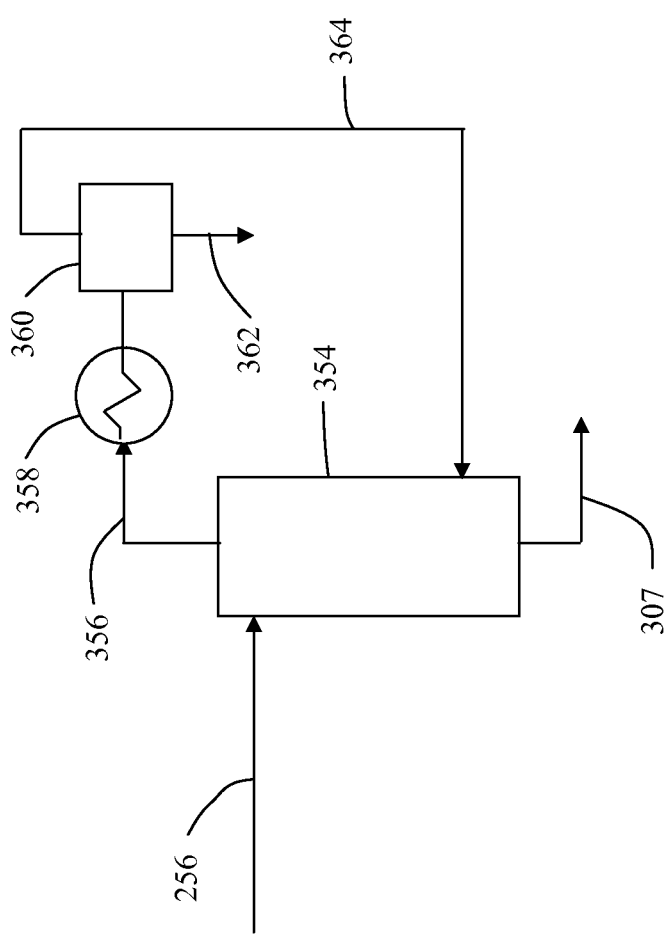
Figure 12. Schematic for Stripping Process

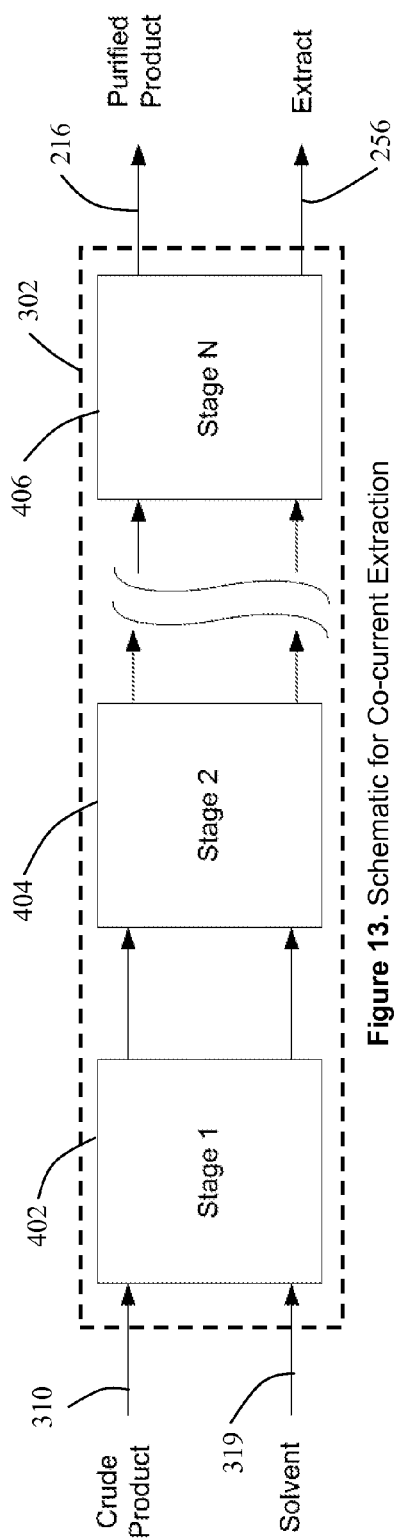
Figure 13. Schematic for Co-current Extraction
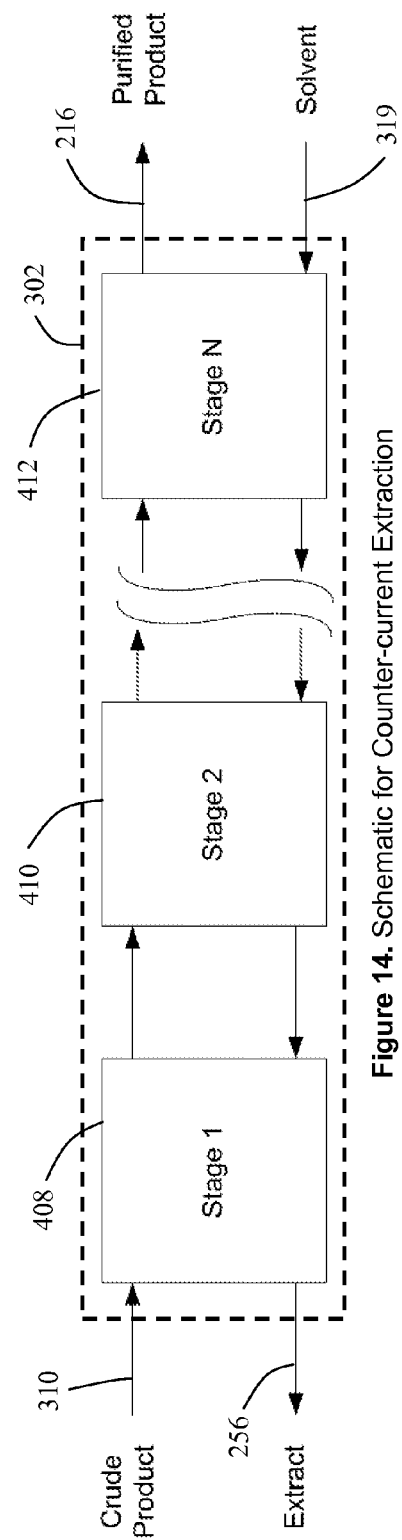
Figure 14. Schematic for Counter-current Extraction

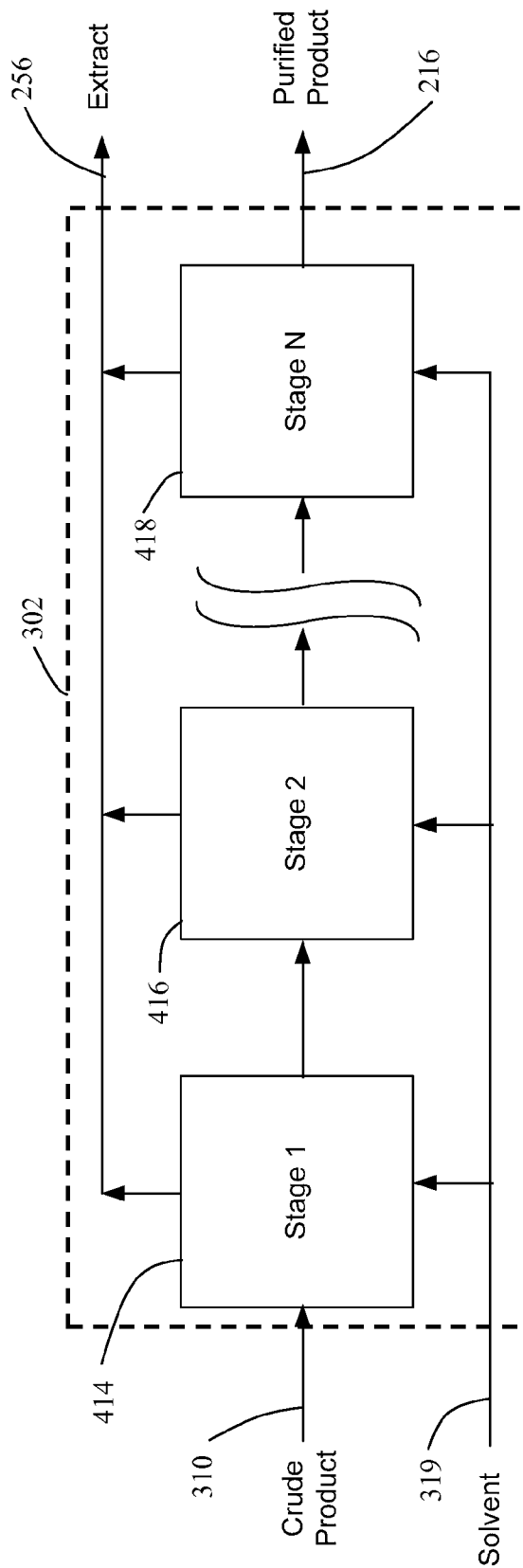
Figure 15. Schematic for Cross-flow Extraction

ETHYL ACETATE PRODUCTION

CROSS-REFERENCE TO RELATED APPLICATIONS

This application is a continuation-in-part of and claims priority to U.S. patent application Ser. No. 12/925,460 filed on Oct. 20, 2010, now U.S. Pat. No. 8,558,025, to Sagar B. Gadewar and entitled "Ethyl Acetate Production," which is a Non-Provisional application of and claims priority to U.S. Provisional Application No. 61/253,349, filed Oct. 20, 2009 to Sagar B. Gadewar and entitled "Ethyl Acetate Production," both of which are incorporated herein by reference in their entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

The following discussion is provided solely to assist the understanding of the reader, and does not constitute an admission that any of the information discussed or references cited constitute prior art to the present invention.

Ethyl acetate can be produced from acetaldehyde according to the Tischenko reaction:

$$2CH_3CHO \leftrightarrow CH_3COOC_2H_5$$

When acetaldehyde is produced from ethanol, ethyl acetate can be produced from ethanol according to the following reaction:

$$2C_2H_5OH \leftrightarrow CH_3COOC_2H_5 + 2H_2$$

Alternately, ethanol can react with acetaldehyde according to the following reaction:

$$C_2H_5OH + CH_3CHO \leftrightarrow CH_3COOC_2H_5 + H_2$$

Conversion of primary alcohols into esters and ketones using copper catalyst is described by K. Takeshita in the Bulletin of the Chemical Society of Japan, (1978) vol. 51(9), pp 2622-2627.

U.S. Pat. No. 4,996,007 describes a process for the oxidation of primary alcohols to aldehydes, esters and acids. A primary alcohol is reacted with oxygen, with a catalyst selected from ruthenium, rhodium, platinum, palladium, rhenium and mixtures thereof, with the option of quaternary C1 to C20 alkyl ammonium co-catalyst, and dihydrodihydroxynaphthalene, dihydroxyanthracene or a mixture thereof as an oxygen activator.

In U.S. Pat. No. 4,220,803 catalytic dehydrogenation of ethanol for the production of acetaldehyde and acetic acid using a supported copper oxide essentially free of barium is proposed.

U.S. Pat. No. 4,052,424 suggested a silver-cadmium alloy catalyst for use in production of alkyl alkanoate esters, by contacting a primary alkanol in the vapor phase with the catalyst at a temperature of between about 250° C. and 600° C.

In U.S. Pat. No. 4,440,946 there is described a process for producing a carboxylate ester which comprises contacting a mixture of alcohol and aldehyde in the vapor phase with a co-precipitate composition comprising silver-cadmium-zinc-zirconium which is substantially in the free metal form.

Use of the Tischenko reaction for the production of mixed esters from aldehydes is described in U.S. Pat. No. 3,714,236.

U.S. Pat. No. 5,334,751 describes production of ethyl acetate by reaction of ethanol and oxygen in the presence of a solid catalyst that contains crystalline $TiP_2O_7$ and has the formula $Pd_aM_bTiP_cO_x$, where M is Cd, Au, Zn, Tl, or an alkali metal or alkaline earth metal, a is 0.0005-0.2, b is 0.3a, c is 0.5-2.5, x has a value to satisfy the valencies, and Ti and P of the crystalline $TiP_2O_7$ represent part of the crystalline $TiP_2O_7$.

BR-A-91/04652 describes pre-treatment of a palladium on a silica carrier catalyst for production of ethyl acetate by direct oxidation of ethanol with air.

Production of esters from primary alcohols by dehydrogenation using bromous acid or a salt thereof in acid medium is described in JP-A-59/025334.

In SU-A-362814 there is described a process for production of ethyl acetate by dehydrogenation of ethanol at 180° C. to 300° C. in the presence of a copper catalyst containing zinc as an activator with an ethanol feed rate of 250 to 700 liters per liter of catalyst per hour.

The dehydrogenation of ethanol to form ethyl acetate is described in GB-A-287846. This proposes use of a dehydrogenating agent, such as a copper catalyst, a temperature of from 250° C. to 500° C., and a pressure of more than 10 atmospheres (1.013×10⁶ Pa).

Vapor phase contact of ethanol at a temperature above its critical temperature with a catalyst comprising copper and a difficultly reducible oxide, such as zinc oxide or manganese oxide, is proposed in GB-A-312345, use of a temperature of 375° C. and a pressure of 4000 psi (27.58 Mpa) being suggested.

GB-A-470773 teaches a process for conversion of ethanol to ethyl acetate by dehydrogenating ethanol over a catalyst consisting of a reduced metal, for example, copper on infusorial earth with 10% uranium oxide as promoter, maintained at a temperature of 220° C. to 260° C., removing by condensation some of the gas-vapor product rich in hydrogen resulting from the reaction, and returning the gaseous remainder rich in hydrogen to the catalyzing zone.

EP-A-0151886 describes a process for the preparation of C2+ esters of alkyl carboxylic acids from C2+ primary alcohols which comprises contacting a vaporous mixture containing a primary C2+ alkanol and hydrogen in an alkanol:hydrogen molar ratio of from 1:10 to about 1000:1 at a combined partial pressure of alkanol and hydrogen of from about 0.1 bar (103 Pa) up to about 40 bar (4×10⁶ Pa) and at a temperature in the range of from about 180° C. to about 300° C. in a catalytic reaction zone with a catalyst consisting essentially of a reduced mixture of copper oxide and zinc oxide, and recovering a reaction product mixture containing a primary C2+ alkyl ester of an alkyl carboxylic acid which ester contains twice as many carbon atoms as the primary C2+ alkanol.

In EP-A-0201105 there is described a method for converting primary alcohols, such as ethanol, to their corresponding alkanoate esters which involves the regulation of the mole feed ratio of hydrogen gas to alkanol in the reaction zone of a copper-chromite containing catalyst.

One method of separating ethyl acetate from ethanol and water involves extractive distillation with an extractive agent comprising polyethylene glycol and dipropylene glycol, diethylene glycol, or triethylene glycol as described in U.S. Pat. No. 4,569,726 or with an extractive agent containing dimethyl sulphoxide as described in U.S. Pat. No. 4,379,028.

Separation of ethyl acetate from a composition comprising ethyl acetate, ethanol and water is described in JP-A-05/186392 by feeding the composition to a distillation column to obtain a quasi-azeotropic mixture comprising ethyl acetate, ethanol and water, condensing it, separating the condensate into an organic layer and an aqueous layer, returning the organic layer to the column, and recovering ethyl acetate as a bottom product from the column.

EP-A-0331021 describes how carbonylation of olefins to produce monocarboxylate esters causes formation of aldehydes and acetals as byproducts. Monocarboxylate esters produced in this way are subjected to a three step purification process involving treatment with a strongly acidic agent, followed by hydrogenation and distillation. The initial treatment with a strongly acidic agent is intended to convert acetals to vinyl ethers and aldehydes and acetals to aldols. The subsequent hydrogenation step then converts these compounds to byproducts which are more easily separated from the desired monocarboxylate ester.

EP-A-0101910 contains a similar disclosure regarding carbonylation of olefins to give monocarboxylate esters. It proposes treatment of the monocarboxylate ester with hydrogen at elevated temperature in the presence of an acidic ion exchanger or zeolite doped with one or more metals of Group VIII of the Periodic Table, followed by hydrogenation. It is stated that acetals present as byproducts are converted to vinyl ethers which are converted by hydrogenation to low boiling esters or the aldehydes and acetals are converted to high boilers by an aldol reaction. Unsaturated ketones are converted to saturated ketones.

U.S. Pat. No. 4,435,595 describes the use of reactive distillation to produce high-purity methyl acetate, by esterifying methanol and acetic acid. The process provides for the use of acetic acid and methanol which flow in countercurrent through a single reactive distillation column in the presence of an acid catalyst. The acetic acid, in addition to being a reagent, also acts as an extracting agent for the non-reacted methanol and for the water which has been produced. Therefore, the methyl acetate is separated continuously from the acetic acid and removed from the top of the column.

SUMMARY

In an embodiment, a method of purifying an ethyl acetate stream comprises contacting an inlet stream with a solvent, transferring at least a portion of the impurity compound from the inlet stream into the solvent to form an extract and a purified product, separating the extract from the purified product, separating the portion of the impurity compound from the extract, forming an impurities stream and a regenerated solvent, and recycling at least a portion of the regenerated solvent to contact the inlet stream. The inlet stream comprises ethyl acetate and an impurity compound, and the extract comprises the solvent and the portion of the impurity compound transferred from the inlet stream.

In an embodiment, a reactive distillation system for producing high purity ethyl acetate from ethanol comprises a reactive distillation column, an extraction unit, and a stripping unit. The reactive distillation column comprises a dehydrogenation catalyst, an ethanol inlet configured to pass an ethanol feed over the dehydrogenation catalyst, a top product gaseous hydrogen removal passage, and a bottoms product liquid ethyl acetate removal passage. The extraction unit is configured to receive a liquid ethyl acetate product stream from the reactive distillation column through the bottoms product liquid ethyl acetate removal passage, contact a liquid solvent feed stream with the liquid ethyl acetate product stream, provide an extract stream comprising a portion of any impurities in the liquid ethyl acetate product stream, and provide a purified product stream. The stripping unit is configured to receive the extract stream from the extraction unit, separate the portion of the impurities from the extract stream, provide an outlet impurities stream, and provide a regenerated solvent stream back to the extraction unit as at least a portion of the liquid solvent feed stream.

In an embodiment, a reactive distillation process producing high purity ethyl acetate from ethanol comprises feeding a feed stream comprising ethanol to a reactive distillation column, contacting the ethanol with a catalyst, dehydrogenating ethanol over the catalyst in the liquid phase during the distillation process, removing ethyl acetate during the distillation process as a bottoms product, and removing hydrogen during the distillation process as a top product.

These and other features will be more clearly understood from the following detailed description taken in conjunction with the accompanying drawings and claims.

BRIEF DESCRIPTION OF THE DRAWINGS

For a more complete understanding of the present disclosure and the advantages thereof, reference is now made to the following brief description, taken in connection with the accompanying drawings and detailed description.

FIG. 11 illustrates a schematic flow diagram of a product separation system according to another embodiment.

FIG. 12 illustrates a schematic flow diagram of a stripping section according to another embodiment.

FIG. 13 illustrates a schematic co-current extraction flow scheme according to an embodiment.

FIG. 14 illustrates a schematic counter-current extraction flow scheme according to an embodiment.

FIG. 15 illustrates a schematic cross-current extraction flow scheme according to an embodiment.

DETAILED DESCRIPTION

Figure 1:
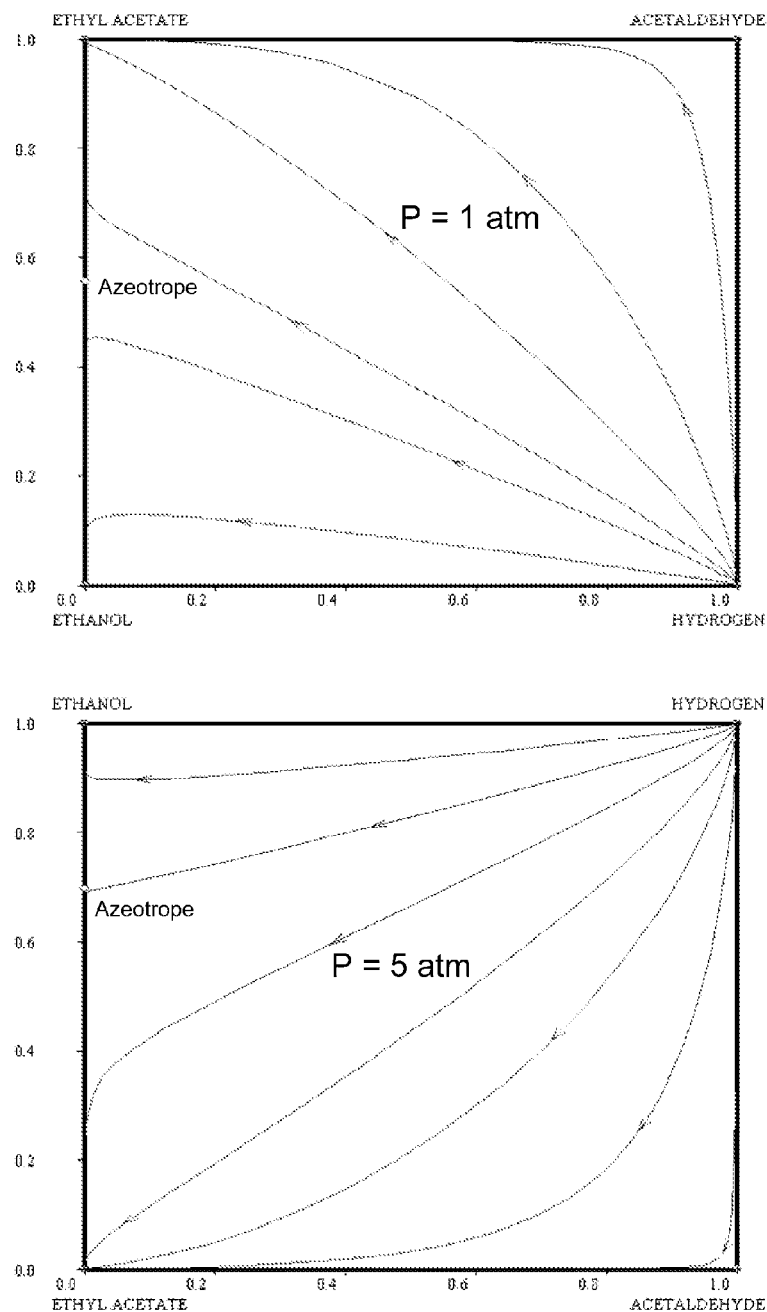
FIG. 1 shows reactive residue maps for conversion of ethanol to ethyl acetate at pressures of 1 and 5 atmospheres (atm) for an embodiment.

A reactive distillation system and process are disclosed herein for producing high purity ethyl acetate from ethanol. This process is beneficial as it provides an improved commercial method of upgrading ethanol to ethyl acetate, a more valuable product. This improved commercial process may be used where there is a supply and/or a surplus supply of ethanol. Further, this process reduces and/or eliminates the need for a separate acetaldehyde or acetic acid plant to provide the precursors for the ethyl acetate production process. The raw material may comprise only ethanol, which may present an advantage relative to other processes requiring multiple feedstocks. In addition, bio-derived ethanol may be used to allow the process to be operated from renewable ethanol sources. Further, the present system and method may utilize base-metal catalysts, which may be less expensive than the precious metal based catalysts of other ethyl acetate production routes. Such catalysts can comprise copper, and may be composed of copper oxide mixed with one or more additional metals and/or metal oxides. The present systems and methods may allow for a one-step ethyl acetate production process, which may be advantageous relative to other processes that require further steps to purify the ethyl acetate product, including a selective removal of 2-butanone, which forms a low boiling azeotrope with ethyl acetate. Each of these advantages may be provided in a process that can also be less expensive than alternative processes by ethyl acetate production from ethanol.

In an embodiment, the present systems and methods can provide a route to ethyl acetate by dehydrogenation and dimerization of ethanol which is capable of yielding high purity ethyl acetate from ethanol feed streams containing significant amounts of byproducts or impurities. One issue in the production of ethyl acetate by dehydrogenation of ethanol is that the reaction product mixture is commonly a complex mixture including esters, alcohols, aldehydes and ketones. From a distillative separation point of view, the mixture is further complicated due to the presence of azeotropes. The reaction product mixtures commonly contain components with boiling points close to ethyl acetate (such as n-butyraldehyde and/or butan-2-one), including components which can form azeotropes with ethyl acetate, and/or other components of the mixture. This may present a challenge when high purity ethyl acetate is desired.

In chemical processing, chemical reaction and the purification of the desired products by distillation may be carried out sequentially. The performance of this chemical process structure may be improved by the integration of reaction and distillation in a single multifunctional process unit. This integration concept is called "reactive distillation." As advantages of this integration, chemical equilibrium limitations may be overcome, higher selectivities may be achieved, the heat of reaction may be used in situ for distillation, auxiliary solvents may be avoided, and/or azeotropic and/or closely boiling mixtures may be more easily separated. Increased process efficiency and reduction in overall capital costs may result from the use of this approach.

A reactive distillation system comprises at least one separator and/or reactor (e.g., a distillation tower, side reactor, etc.) in which a reaction is occurring. In general, suitable separators may include any process equipment suitable for separating at least one inlet stream into a plurality of effluent streams having different compositions, states, temperatures, and/or pressures. For example, the separator may be a column having trays, packing, or some other type of complex internal structure. Examples of such columns include scrubbers, strippers, absorbers, adsorbers, packed columns, and distillation columns having valve, sieve, or other types of trays. Such columns may employ weirs, downspouts, internal baffles, temperature control elements, and/or pressure control elements. Such columns may also employ some combination of reflux condensers and/or reboilers, including intermediate stage condensers and reboilers. In an embodiment, the reactive distillation system described herein may comprise a distillation tower having at least one catalyst disposed therein. The catalyst may take a variety of forms, and the separator may comprise any combination of catalyst and separator structures. For example, the separator may comprise sequential layers of catalysts and distillation packing and/or the packing may comprise catalytic elements such as pellets that act as a structured packing. In some embodiments, the reactive distillation system described herein may comprise a distillation tower comprising one or more side reactors comprising at least one catalyst disposed therein, where the one or more side reactors are coupled to and are in fluid communication with the distillation tower As indicated above, the present systems and methods provide for the production of ethyl acetate from ethanol at a relatively low cost, along with a plant or distillation system with significantly reduced complexity using reactive distillation. The present disclosure further provides an improved process for the production of high purity ethyl acetate from ethanol, or from a feedstock comprising a major proportion of ethanol and a minor proportion of impurities such as iso-propanol and iso-butanol. While not commonly present in ethanol feed streams, impurities that can poison the particular catalyst used should be limited, avoided and/or removed. For example, sulfur or nitrogen heterocyclic compounds can frequently act as catalyst poisons and, if present, should be removed before introducing the ethanol feed stream to the reactive distillation column. In an embodiment, the ethanol feed may comprise water. The presence of water in the ethanol feed does not severely reduce the performance of the catalysts, which can tolerate up to 5% water by weight in the ethanol. Ethanol conversion is reduced when using an ethanol source with significant water content, but the reaction selectivity increases. The use of an ethanol feed comprising a small amount of water may be advantageous by allowing for the use a potentially less expensive ethanol source in the form of the ethanol/water azeotrope (about 4.4% water by weight). The effects of water are demonstrated in the Examples described herein.

Ethyl acetate can be produced from ethanol according to the following reactions:

$$C_2H_5OH \leftrightarrows CH_3CHO + H_2$$

$$CH_3CHO + C_2H_5OH \leftrightarrows CH_3COOC_2H_5 + H_2$$

The Tishchenko reaction may also provide a potential reaction route for the production of ethyl acetate from ethanol:

$$C_2H_5OH \leftrightarrows CH_3CHO + H_2$$

$$2CH_3CHO \leftrightarrows CH_3COOC_2H_5$$

In an embodiment, ethanol reacts in a single continuous reactive distillation column which provides sufficient residence time to achieve a relatively high conversion of ethanol. In an embodiment, the reactive distillation column may be configured to provide a conversion of ethanol of at least about 10% and a selectivity of at least about 60%, as described in more detail herein. Table 1 shows the effect of pressure on the boiling point of the pure components and azeotrope in the mixture. The azeotrope between ethanol and ethyl acetate is substantially avoided above a pressure of 13 atm.

TABLE 1

Boiling point of reaction components.

| | Boiling Point, C. | | | | | |
|---|---|---|---|---|---|---|
| | P = 1 atm | P = 5 atm | P = 10 atm | P = 20 atm | P = 30 atm | P = 40 atm |
| Hydrogen | −161 | −137.6 | −123.7 | −106.5 | −94.3 | −84.5 |
| Acetaldehyde | 20.4 | 71.9 | 101.1 | 136.4 | 160.7 | 180 |
| Ethanol | 78.3 | 125.2 | 150.2 | 179 | 198 | 212.7 |
| Ethyl acetate | 77 | 136 | 169.6 | 210.3 | 238.4 | 260.7 |
| Ethanol/Ethyl acetate azeotrope | 71.7 | 123.5 | 150.1 | No Azeo | No Azeo | No Azeo |

Residue curve maps can be used to indicate feasible product compositions for distillation columns. In the presence of reaction along with separation, reactive residue curve maps can be used to determine feasible products from a reactive distillation column. Reactive residue curve maps at a pressure of 1 atm and 5 atm respectively are shown in FIG. 1. The stable nodes in the diagram are ethanol and ethyl acetate, and, therefore, it is possible to design a reactive distillation column where either ethanol or ethyl acetate can be obtained as the bottoms product. Hydrogen is an unstable node in the diagram and can be obtained as the distillate. Acetaldehyde and the ethanol/ethyl acetate azeotrope are saddle points in the diagram.

Figure 2:
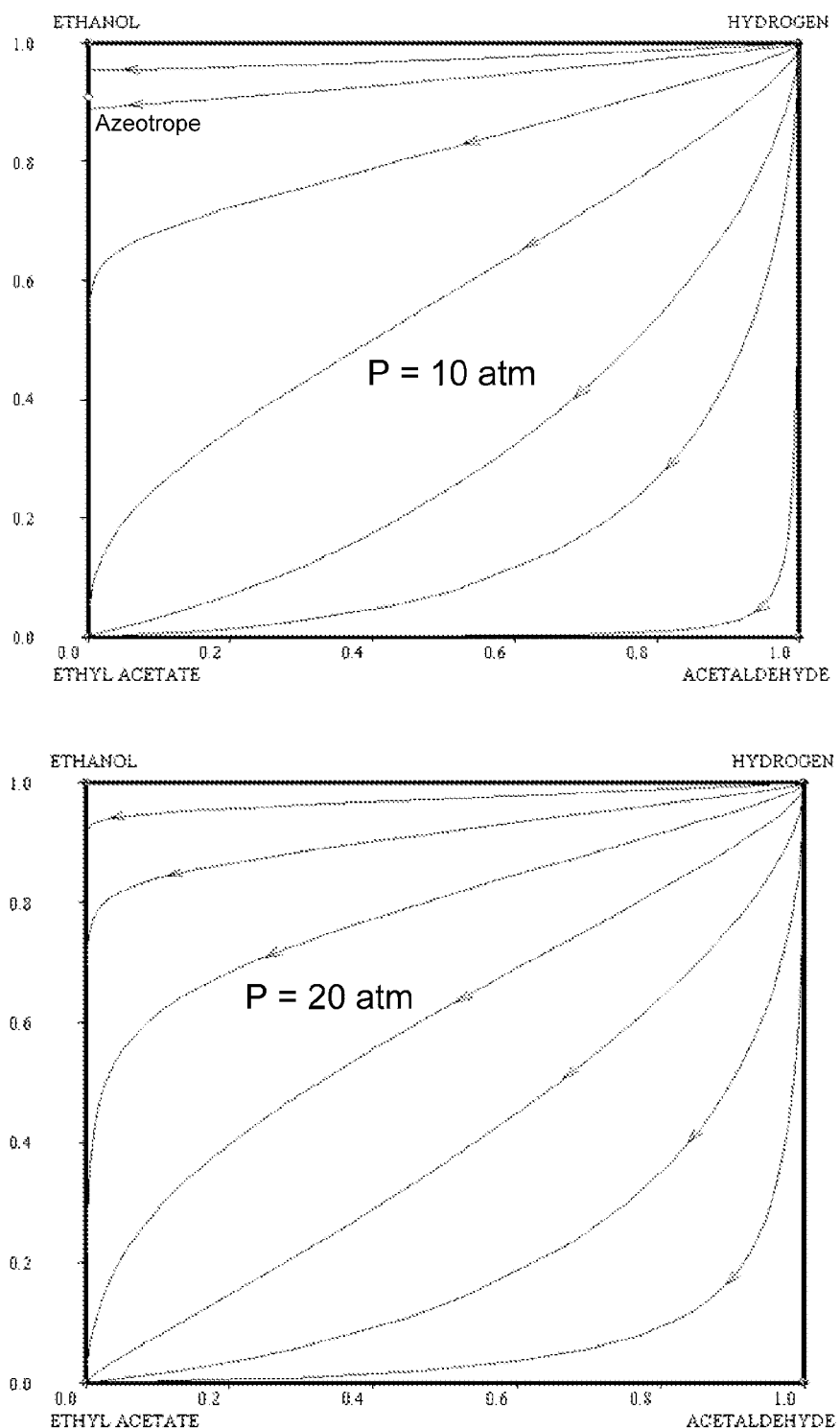
FIG. 2 shows reactive residue maps for conversion of ethanol to ethyl acetate at pressures of 10 and 20 atm for an embodiment.

Reactive residue curve maps at pressures of 10 atm and 20 atm respectively are shown in FIG. 2. The reactive residue curve maps for any pressure above 20 atm are substantially similar to the reactive residue curve map at 20 atm.

In view of the reactive residue maps discussed above, a set of reactive distillation systems effective to produce high purity ethyl acetate from ethanol have been designed. The reactive distillation column can have single or multiple feed locations.

Reactive Distillation Column Configurations

The present systems and methods provide a reactive distillation system in which ethanol may be the sole or primary component of the feed. In some embodiments, the ethanol feed is used in conjunction with a separate, second feed of hydrogen. Reference to a "single feed" to a reactive distillation column means that the column has only one chemical feed stream supplying intended reactant(s) to the column. Nonetheless, such a single feed distillation column may have multiple entry points for the reactant, or recycling feed streams where a part of the reactant liquid or a partial distillate is drawn from the column and fed back into the column at a different point, e.g., to achieve improved separation and/or more complete reaction. A "single ethanol feed" thus refers to a single feed stream, in which ethanol is the sole or at least the primary constituent. In contrast, the term "dual feed" in the context of a distillation column refers to two separate chemical feed streams. For example, in some of the present embodiments, dual feeds are an ethanol feed and a separate hydrogen feed. The term "reactive distillation column" is used conventionally to refer to a distillation column in which both reaction and separation is performed. In this case, the primary and desired reaction is the conversion of two ethanol molecules to one ethyl acetate molecule with release of two hydrogen molecules. Thus, the present invention provides systems and methods for the production of ethyl acetate from ethanol which includes reacting ethanol over a suitable dehydrogenation and/or dimerization catalyst, thereby producing ethyl acetate and hydrogen.

In an embodiment, a single reactive distillation column is used. Hydrogen gas is removed (e.g., continuously) from the top of the reactive distillation column as an overhead stream. Ethyl acetate is removed (e.g., continuously) from the bottom of the column as a bottoms stream. Optionally, contaminating byproducts present following reaction of the ethanol over the dehydrogenation catalyst can be separated from the ethyl acetate product stream. Various byproduct separation schemes are possible including, but not limited to, reacting the byproducts in the product stream over a suitable hydrogenation catalyst in the lower part of the column or in a separate hydrogenation reactor. The hydrogenation can convert difficult to separate byproducts into species which are easier to separate from the ethyl acetate. Consequently, the process can also include purifying the ethyl acetate by distilling out resulting hydrogenated byproducts. In some embodiments, an extraction process may be used selectively remove one or more byproducts from the ethyl acetate products stream. Consequently, the process may also include purifying the ethyl acetate by contacting the product stream with an extractant, which can be regenerated and recycled to the extraction system.

In an embodiment, the reactive distillation column is configured for the dehydrogenation of ethanol with the formation of ethyl acetate. The reaction is accomplished by passing the ethanol feed stream over a dehydrogenation catalyst under conditions where ethyl acetate is formed and hydrogen and ethyl acetate are withdrawn as top and bottoms products respectively. Such product draws drive the thermodynamics of the process toward the desired products. In its simplest form, a reactive distillation system may comprise a reactor vessel operating with a liquid phase reaction in which hydrogen and/or other light gases are removed as the overhead product and a reaction product is removed as the bottoms product. Such a system may comprise a batch reactor in which hydrogen is removed during the reaction and the liquid product is removed after completion of the reaction to a desired degree of conversion.

Figure 3:
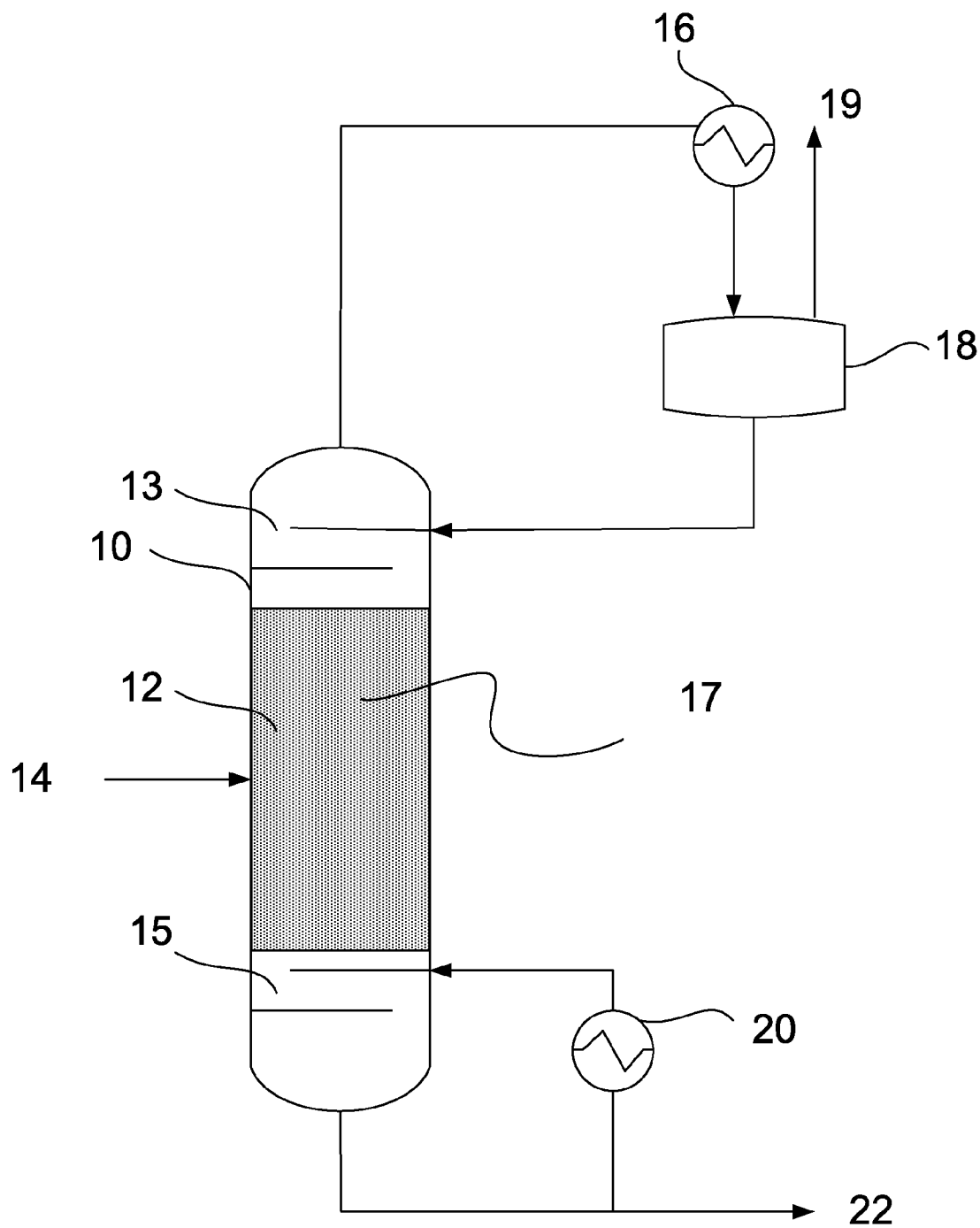
FIG. 3 shows a simplified schematic of a reactive distillation system according to an embodiment.

An embodiment of a reactive distillation column with a single feed of ethanol is shown schematically in FIG. 3 can produce hydrogen as a distillate and ethyl acetate as a bottoms product. Column 10 contains a generally central catalyst zone 12, and usually will include a top stage or non-reactive rectifying section 13 and a bottom stage or non-reactive stripping section 15. Ethanol feed 14 is commonly fed to the middle part of the reactive distillation column. Distillate removed at the top of the column is passed through a partial condenser 16, and hydrogen is separated from lower boiling constituents in reflux tank 18. The hydrogen may leave the system as an overhead product stream 19, which in an embodiment may comprise trace amounts of additional components including ethanol, ethyl acetate, and/or one or more reaction byproducts. The condensed lower boiling constituents (i.e., reflux), or at least some portion thereof, can be cycled back to the column for further reaction and/or separation. The bottoms product can be passed through reboiler 20, where a portion of the bottoms product is evaporated and added back to the bottom of the column. The remaining bottoms product may pass out of the system as product stream 22. Alternatively, only a portion of the bottoms product may be passed through reboiler 20, with the vapor portion passing back to the bottom of the column and the remainder of the bottoms product being combined with any bottoms product bypassing the reboiler 20 and passing out of the system as product stream 22 for further processes and/or use as a final product. The product stream 22 may comprise the ethyl acetate produced in the column along with unreacted ethanol and potentially any side products produced by the reaction. The column reflux and reboil ratios are maintained such that essentially pure ethyl acetate is obtained as the bottoms product. In an embodiment, the bottoms product stream 22 may comprise greater than about 90%, greater than about 95%, greater than about 96%, greater than about 97%, greater than about 98%, greater than about 99%, or greater than about 99.5% ethyl acetate by weight.

During operation, the reactants and products flow through the reactor/column reacting and flashing along the length of the reactor/column. In an embodiment, the reaction of the reactants and/or products may occur in the catalyst zone 12, and the reactions may occur in the vapor and/or liquid phase. While not intending to be limited by theory, it is believed that the dehydrogenative dimerization of ethanol to ethyl acetate may occur over the dehydrogenation and dimerization catalysts described herein in the liquid phase. It has not been previously recognized that the dehydrogenation and dimerization conversion of ethanol to ethyl acetate would occur in the liquid phase. The use of a liquid phase reaction may allow for reactive distillation to be effectively used for converting ethanol into ethyl acetate and hydrogen. Specific catalysts useful in the reactive distillation systems and methods disclosed herein are discussed in more detail below. Ethyl acetate and hydrogen are produced due to the reaction over the dehydrogenation and dimerization catalyst. Byproducts including, but not limited to, aldehydes, such as acetaldehyde, n-butyraldehyde, and/or crotonaldehyde; ethers, such as ethyl ether and n-butyl ether; ethyl acetate; ketones such as 2-butanone, acetone; and other alcohols, such as isobutanol, 2-butanol, 2-ethylbutanol, n-hexanol, and/or 2-ethylhexanol may also be produced during the reaction. The removal of the overhead stream 19 comprising hydrogen, which may occur by flashing, increases the extent of reaction. In general, the hydrogen concentration increases from the middle part of the column towards the top of the column. At pressures of about 13 bar or lower, as ethyl acetate is formed from the reactants, an azeotrope between ethyl acetate and ethanol occurs. This azeotrope may result in the overhead product 19 that leaves the top of the reactive distillation column 10 containing ethanol/ethyl acetate and/or acetaldehyde in addition to hydrogen. A partial condenser 16 allows hydrogen to be removed as a distillate, while acetaldehyde and ethanol are recycled back to the top of the reactive distillation column. At a pressure above about 13 atm, the ethyl acetate and ethanol azeotrope disappears, which improves the operation of the reactive distillation column.

The column 10 can be operated at any suitable pressure between about 1 atm and about 80 atm. In an embodiment, the column 10 may be operated at a pressure ranging from about 1 atm to about 5 atm, about 5 atm to about 10 atm, about 7 atm to about 12 atm, about 13 atm to about 15 atm, about 13 atm to about 20 atm, about 15 atm to about 20 atm, about 15 atm to about 30 atm, about 20 atm to about 30 atm, about 20 atm to about 50 atm, about 30 atm to about 40 atm, about 40 atm to about 50 atm, or about 50 atm to about 60 atm, about 60 atm to about 70 atm, about 60 atm to about 80 atm, or about 70 atm to about 80 atm. In an embodiment, the reactive distillation is performed at a pressure where ethanol-ethyl acetate azeotrope is not present. The temperature profile in the column is dictated by the mixture boiling point along the height of the column. In an embodiment the temperature within the column may range from about 100° C. to about 350° C., alternatively about 150° C. to about 250° C. The column 10 may comprise any number of stages equivalent to a number of theoretical stages sufficient to effect the reaction and separation of ethyl acetate to a desired purity. In an embodiment, the number of stages or the number of height equivalents of a theoretical plate (HETP) may range from about 1 to about 100, including for example from about 1 to about 10, about 10 to about 20, about 10 to about 50, about 20 to about 30, about 20 to about 70, about 30 to about 40, about 30 to about 50, about 30 to about 100, about 50 to about 70, about 50 to about 100, or about 70 to about 100. As described in more detail below, a relatively high conversion of ethanol to products can be achieved by the counter-current flow of reactants and products in addition to overcoming the reaction equilibrium by removal of products through the concurrent distillation within the column 10.

Figure 4:
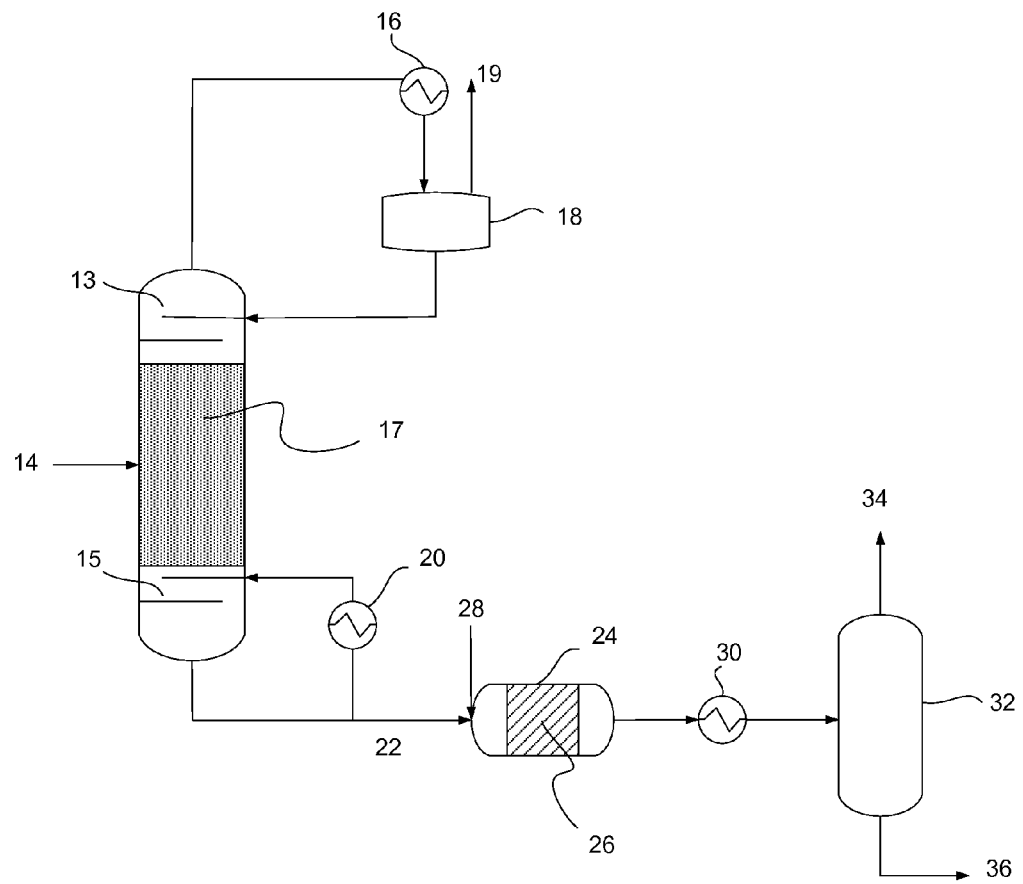
FIG. 4 shows a simplified schematic of a reactive distillation system according to another embodiment.

In an embodiment, the systems and methods may also include hydrogenating contaminants or reaction byproducts in the bottoms stream or in the reacted fluid after it has passed over the dehydrogenation catalyst and separating the hydrogenated contaminants or byproducts from the ethyl acetate. As noted above, aldehydes and/or ketones such as n-butyraldehyde and butan-2-one may be produced as byproducts in the reaction. These byproducts boil at temperatures close to the boiling point of ethyl acetate and may be difficult to separate from ethyl acetate. FIG. 4 shows a process schematic where the bottoms product 22 from the reactive distillation column 10 illustrated in FIG. 3 is sent to a hydrogenation reactor 24 comprising a hydrogenation catalyst 26 with a hydrogen co-feed 28. Suitable hydrogenation catalyst(s) may comprise various components and are described in more detail herein. At least a portion of the n-butyraldehyde and/or butan-2-one impurities and/or byproducts can be hydrogenated and can then be separated using a separator 32. The separator 32 may comprise any of the types of separators described herein with respect to the reactive distillation system. Alternatively or in addition to the separators already described, the separator 32 may be a phase separator, which is a vessel that separates an inlet stream into a substantially vapor stream and a substantially liquid stream, such as a knock-out drum, flash drum, reboiler, condenser, or other heat exchanger. Such vessels also may have some internal baffles, temperature control elements, and/or pressure control elements, but generally lack any trays or other type of complex internal structure commonly found in columns. The separator also may be any other type of separator, such as a membrane separator. In a specific embodiment, the separator is a knockout drum. Finally, the separator may be any combination of the aforementioned separators arranged in series, in parallel, or combinations thereof. In an embodiment, separator 32 comprises a distillation column. The outlet of the hydrogenation reactor 24 may be passed through a heat exchanger 30 (e.g., a condenser) and cooled before entering the separator 32. The heat exchanger 30 may be any equipment suitable for heating or cooling one stream using another stream. Generally, the heat exchanger 30 is a relatively simple device that allows heat to be exchanged between two fluids without the fluids directly contacting each other. Examples of suitable heat exchangers 30 include, but are not limited to, shell and tube heat exchangers, double pipe heat exchangers, plate fin heat exchangers, bayonet heat exchangers, reboilers, condensers, evaporators, and air coolers. In the case of air coolers, one of the fluids comprises atmospheric air, which may be forced over tubes or coils using one or more fans.

The bottoms product stream 36 from the separator 32 may comprise ethyl acetate and may have a purity of greater than about 90%, greater than about 95%, greater than about 96%, greater than about 97%, greater than about 98%, greater than about 99%, or greater than about 99.5% ethyl acetate by weight. Unconverted hydrogen and the hydrogenated byproducts may be removed as an overhead product 34, and may be used, for example, as fuel or a feed to one or more processes. In an embodiment, the separator 32 may be operated between a pressure of 1 atm and 80 atm.

In an embodiment, the bottoms product stream 36 may pass to another separator. The separator may then separate the bottoms product stream into an ethyl acetate stream and a byproduct stream comprising one or more heavier hydrogenation products produced in the hydrogenation reactor 26. This separation scheme may allow the resulting ethyl acetate stream to have a purity of greater than about 90%, greater than about 95%, greater than about 96%, greater than about 97%, greater than about 98%, greater than about 99%, or greater than about 99.5% ethyl acetate by weight.

Figure 5:
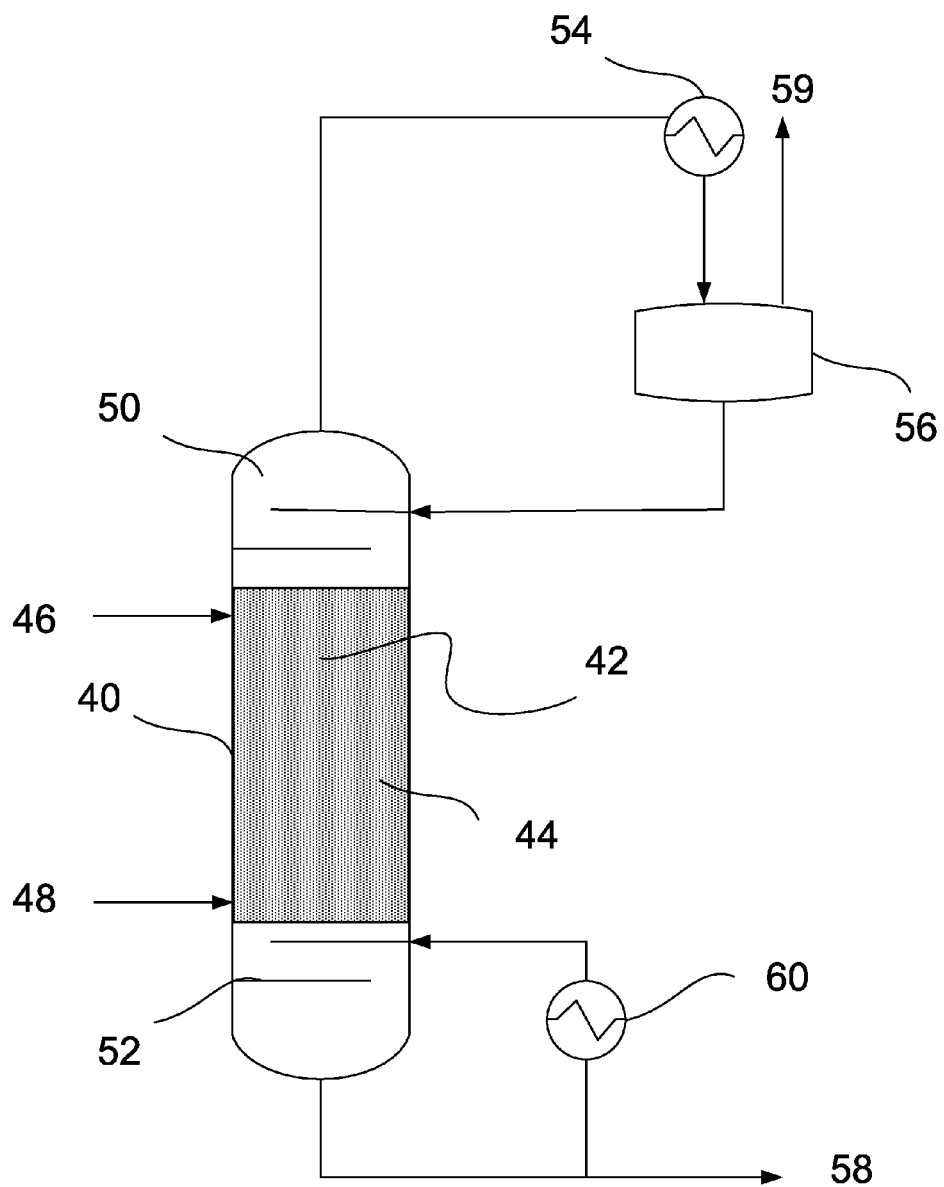
FIG. 5 shows a simplified schematic of a reactive distillation system according to still another embodiment.

In another embodiment of the invention, the reactive distillation column has two feeds. Ethanol may be fed to the upper part of the column (upper feed), and hydrogen may be fed to the lower part of the column (lower feed). A schematic for the double feed reactive distillation column is schematically illustrated in FIG. 5. This system includes column 40 containing catalyst 42 in catalyst zone 44, and commonly may include a top stage or non-reactive rectifying section 50 and a bottom stage or non-reactive stripping section 52. In the illustrated system, ethanol feed 46 is delivered at or near the top of the catalyst zone 44, and the hydrogen feed 48 is delivered at or near the bottom of catalyst zone 44. It should be recognized columns can be designed with the ethanol feed 46 location in other locations, e.g., within the catalyst zone 44 but above the hydrogen feed 48, such as from the approximate middle of the catalyst zone 44 to the top of the column 40. Similarly, columns with the hydrogen feed 48 in other locations can also be designed, e.g., with the hydrogen feed 48 from the approximate middle of the catalyst zone 44 to the bottom of the column 40 or even higher within the catalyst zone 44 but below the ethanol feed 46. In an embodiment, the ethanol feed 46 and the hydrogen feed 48 are separated sufficiently to allow byproduct hydrogenation to be substantially completed before hydrogen from the feed reaches substantial concentrations of ethanol being dehydrogenated. Ethanol reacts over the catalyst producing ethyl acetate and hydrogen. Examples of suitable dehydrogenation and dimerization catalysts are described in more detail herein.

Due to boiling point differences, hydrogen moves towards the top of the column 40 and ethyl acetate moves towards the bottom of the column 40. Acetaldehyde may be produced during the reaction and may move up in the column 40. At least a portion of the acetaldehyde, if present, can be condensed in condenser 54 (e.g., a partial condenser, or a total condenser), passed through reflux tank 56, and recycled back to column 40 as reflux. A product stream 59 comprising hydrogen is taken out as distillate from the reflux tank 56. A part of the bottom draw is taken out as the ethyl acetate product stream 58, while the remaining part is passed through reboiler 60 to be recycled to the column 40. In an embodiment, the bottom draw may be passed through a reboiler (e.g., similar to reboiler 60) and optionally passed to a separator where the vapor portion may pass to the column 40 while at least a portion of the remainder is taken out as the ethyl acetate product stream 58. The stream passing through the reboiler 60 provides the evaporation effect and vapor flow for operating the column 40. The product stream 58 may comprise the ethyl acetate produced in the column along with unreacted ethanol and potentially any side products produced by the reaction.

Byproducts such as n-butyraldehyde and butan-2-one produced in the reaction may have boiling points close to the boiling point of ethyl acetate. The lower hydrogen feed 48 is useful in hydrogenating the by-products to produce components that can be separated easily from ethyl acetate. The ratio of the hydrogen feed to the ethanol feed can beneficially be adjusted to minimize the amount of close boiling byproducts, while not excessively reducing ethyl acetate to ethanol. In an embodiment, the molar ratio of ethanol to hydrogen ranges from about 1:10 to about 1000:1, e.g., from about 1:10 to about 1:1, from about 1:1 to about 5:1, from about 1:1 to about 10:1, from about 5:1 to about 25:1, from about 5:1 to about 50:1, from about 10:1 to about 50:1, from about 10:1 to about 100:1, from about 50:1 to about 200:1, from about 50:1 to about 400:1, from about 100:1 to about 500:1, from about 100:1 to about 1000:1, from about 200:1 to about 1000:1, or from about 500:1 to about 1000:1. Hydrogen product from the reaction leaves at the top of the column. In an embodiment, the column 40 may operate at any of the conditions (e.g., operating pressure, operating temperature, etc.) discussed herein with respect to column 10 in FIG. 3. In addition, the column 40 may have any number of stages, and in an embodiment, the column 40 may have a number of stages as described with respect to column 10 in FIG. 3.

Figure 6:
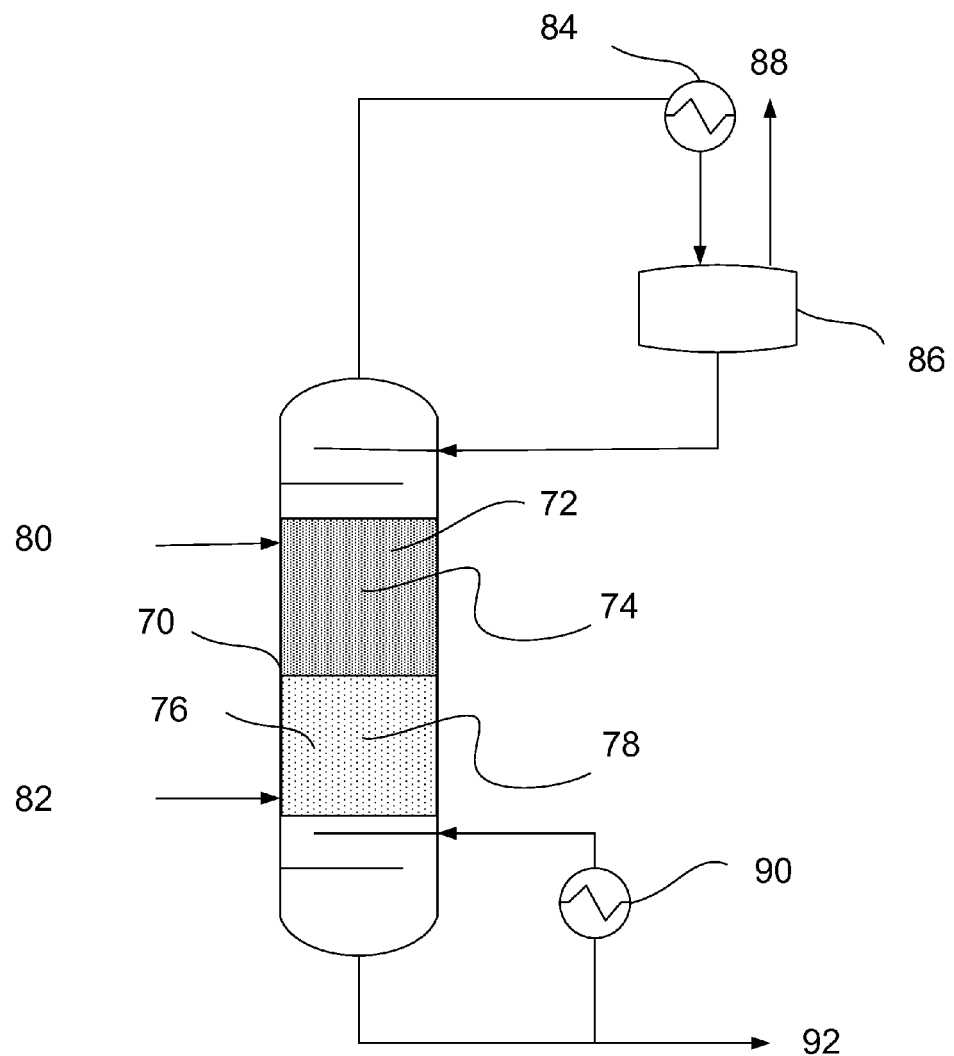
FIG. 6 shows a simplified schematic of a reactive distillation system according to yet another embodiment.

As schematically illustrated in FIG. 6, the reactive distillation column 70 has two feeds 80, 82 and uses two catalyst zones, identified as an upper zone 72 containing Catalyst A 74 and a lower catalyst zone 76 containing Catalyst B 78. Ethanol feed 80 is fed to the upper part of the column 70 (upper feed). Hydrogen feed 82 is fed to the lower part of the column 70 (lower feed). The molar ratio of ethanol to hydrogen may fall within any of the ranges described above with respect to FIG. 5 (e.g., from about 1:10 to about 1000:1, and all sub-ranges). Ethanol may react over the upper catalyst (Catalyst A 74) producing ethyl acetate and hydrogen. Examples of suitable upper catalysts are described in more detail herein with respect to the dehydrogenation and dimerization catalysts. As with previous schematic designs shown, the column 70 will usually include a top stage or non-reactive rectifying section 71 and a bottom state or non-reactive stripping section 79.

Due to boiling point differences, hydrogen moves towards the top of the column 70 and ethyl acetate moves towards the bottom of the column 70. Acetaldehyde may be produced during the reaction and may move up in the column 70. At least a portion of the acetaldehyde, if present, can be condensed in condenser 84 and recycled back to the reaction zone through reflux tank 86. Byproducts such as n-butyraldehyde and butan-2-one produced in the reaction can have boiling points close to the boiling point of ethyl acetate. The lower hydrogen feed is useful in hydrogenating the byproducts over the lower catalyst (Catalyst B) to produce components that can be separated easily from ethyl acetate. Examples of hydrogenation catalysts (Catalyst B) are described in more detail herein. A product stream 88 comprising hydrogen from the reaction leaves at the top of the column 70. A portion of the bottom draw is taken out as the ethyl acetate product stream 92, while the remaining portion is passed through reboiler 90 to be recycled to the column 70. In an embodiment, the bottom draw may be passed through a reboiler (e.g., similar to reboiler 90) and optionally passed to a separator where the vapor portion may pass to the column 70 while at least a portion of the remainder is taken out as the ethyl acetate product stream 92. The stream passing through the reboiler 90 provides the evaporation effect and vapor flow for operating the column 70. The product stream 92 may comprise the ethyl acetate produced in the column along with unreacted ethanol and potentially any side products produced by the reaction. Subsequent purification of product stream 92 comprising ethyl acetate may be needed to remove the hydrogenated byproducts from the ethyl acetate, e.g., using a separator such as that as shown in FIG. 4 as separator 32, which in an embodiment may comprise a distillation column.

In an embodiment, the column 70 may operate at any of the conditions (e.g., operating pressure, operating temperature, etc.) discussed herein with respect to column 10 in FIG. 3. In addition, the column 70 may have any number of stages, and in an embodiment have any number of stages as described with respect to column 10 in FIG. 3.

In the dual feed systems described above with respect to FIGS. 5 and 6, the hydrogen feed should be at a sufficiently low level that it does not significantly adversely affect the dehydrogenation of ethanol in the zone above, while being effective to hydrogenate the undesirable close boiling point byproducts. Feed rates of hydrogen can be adjusted empirically to optimize this balance. Commonly, the ratio of ethanol:hydrogen will be in a range of about 500:1 to 1:1 molar ratio, more commonly about 500:1 to 10:1 or 500:1 to 100:1.

In an embodiment, side reactors can be connected to a reactive distillation column to increase the catalyst holdup for improved reactant conversion. In the side reactor embodiment, the side reactor feed is withdrawn from the distillation column and the reactor effluent is returned back to the same column. An adequate amount of catalyst may be arranged in a side reactor system where traditional reactor types and catalyst structures can be used. Also, the reaction conditions within the side reactor such as temperature can be adjusted independently of those prevailing in the distillation column by appropriate heat exchange. In some embodiments, only the side reactor may comprise one or more catalysts, and the column may operate to separate the outlet of the side reactors. In this embodiment, the column may not contain a dehydrogenation catalyst, or in some embodiments, any catalyst at all.

Figure 7:
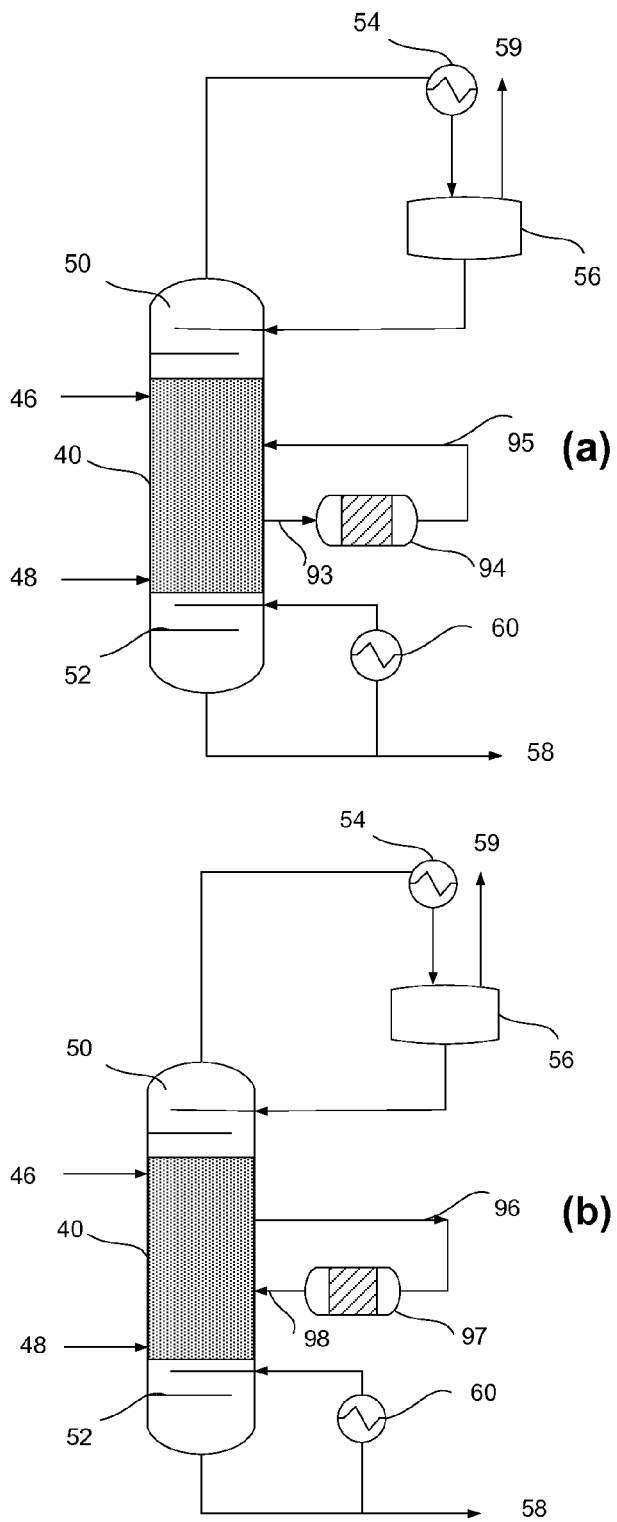
FIGS. 7(a) and 7(b) shows a simplified schematic of a reactive distillation system according to an embodiment.

Schematics for a side reactor reactive distillation column with a single catalyst are shown in FIG. 7. A single side reactor is shown, however, multiple side reactors along the length of the reactive distillation column can be used. FIG. 7(a) shows a configuration where the feed 93 to the side reactor 94 is bottom up and vapor phase. The outlet from side reactor 94 is stream 95 which is sent back to the distillation column 40 at any location in the column 40 above the location of feed 93. FIG. 7(b) shows a configuration where the feed 96 to the side reactor 97 is top down and liquid phase. The outlet from side reactor 97 is stream 98 which is sent back to the distillation column 40 at any location in the column 40 below the location of feed 96. The side reactors 94 and 97 each contain catalyst for converting ethanol into ethyl acetate. Examples of suitable catalysts are described in more detail herein.

The use of a side reactor using a liquid feed may allow for the reaction to occur in the liquid phase. While not intending to be limited by theory, it is believed that the dehydrogenative dimerization of ethanol to ethyl acetate may occur over the dehydrogenation and dimerization catalysts described herein in the liquid phase. As noted above, it has not been previously recognized that the dehydrogenation and dimerization conversion of ethanol to ethyl acetate would occur in the liquid phase. The use of a liquid phase reaction may allow for reactive distillation to be effectively used for converting ethanol into ethyl acetate and hydrogen.

While illustrated as a bottom up vapor phase design and a top down liquid phase design in FIGS. 7(a) and 7(b), the side reactors 94, 97 may also operate bottom up using a liquid phase draw from the column 40 and top down using a vapor phase draw from the column with the appropriate equipment such as pumps, compressors, valves, piping, etc. In an embodiment, the side reactors 94, 97 may be implemented as a single reactor vessel, or as a plurality of reactor vessels arranged in series and/or parallel. In an embodiment, a plurality of side reactors may be implemented as shown in FIGS. 7(a) and 7(b) along the length of the column as needed. In addition, the catalyst in both the column 40 and the side reactor 94 may convert ethanol into ethyl acetate, though the specific catalysts (e.g., catalyst compositions, catalyst forms, and/or catalyst component loadings) in each of the column 40 and the side reactor 94, 97 may be the same or different. Suitable catalysts for converting ethanol into ethyl acetate may be selected based on the expected operating conditions, which may vary between the column 40 and the side reactor 94, 97.

Figure 8:
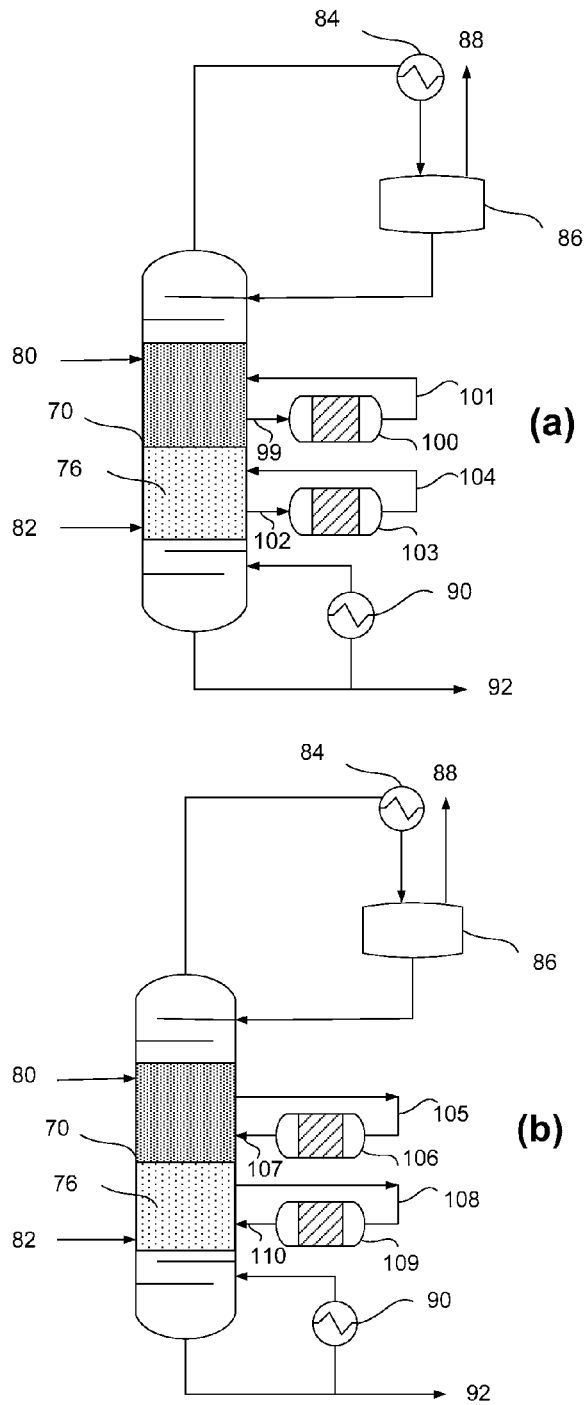
FIGS. 8(a) and 8(b) shows a simplified schematic of a reactive distillation system according to another embodiment.

Schematics for a side reactor reactive distillation with two feeds and using two distinct catalyst zones are shown in FIG. 8. A single side reactor is shown for each catalyst zone in the reactive distillation column 70, however, multiple side reactors along the length of the reactive distillation column 70 can be used for each catalyst zone. FIG. 8 (a) shows a configuration where the top zone feed 99 to the side reactor 100 is bottom up and vapor phase. The bottom zone feed 102 to another side reactor 103 is also bottom up and vapor phase. The outlet from side reactor 100 is stream 101 which is sent back to the distillation column at any location in the column above the location of feed 99. The outlet from side reactor 103 is stream 104 which is sent back to the distillation column at any location in the column above the location of feed 102. FIG. 8 (b) shows a configuration where the top zone feed 105 to the side reactor 106 is top down and liquid phase. The bottom zone feed 108 to another side reactor 109 is also top down and liquid phase. The outlet from side reactor 106 is stream 107 which is sent back to the distillation column at any location in the column below the location of feed 105. The outlet from side reactor 109 is stream 110 which is sent back to the distillation column at any location in the column below the location of feed 108. Examples of suitable catalysts for side reactors 100 and 106 may include any of the dehydrogenation and dimerization catalysts described in more detail herein. Examples of hydrogenation catalysts for side reactors 103 and 109 include any of the hydrogenation catalysts described in more detail herein.

While illustrated as a bottom up vapor phase design and a top down liquid phase design in FIGS. 8(a) and 8(b), the side reactors 100, 103, 106, 109 may also operate bottom up using a liquid phase draw from the column 70 and top down using a vapor phase draw from the column 70 with the appropriate equipment such as pumps, compressors, valves, piping, etc. In an embodiment, the side reactors 100, 103, 106, 109 may be implemented as a single reactor vessel, or as a plurality of reactor vessels arranged in series and/or parallel. In an embodiment, a plurality of side reactors may be implemented as shown in FIGS. 8(a) and 8(b) along the length of the column as needed. In addition, the respective catalysts in the column 70 and/or the side reactors 100, 106 may convert ethanol into ethyl acetate, though the specific catalysts (e.g., catalyst compositions, catalyst forms, and/or catalyst component loadings) in each of the column 40 and the side reactors 100, 106 may be the same or different. Suitable catalysts for converting ethanol into ethyl acetate may be selected based on the expected operating conditions, which may vary between the column 40 and the side reactors 100, 106. Similarly, the respective catalysts in the column 70 and/or the side reactors 103, 109 may comprise hydrogenation catalysts, though the specific catalysts (e.g., catalyst compositions, catalyst forms, and/or catalyst component loadings) in each of the column 70 and the side reactors 103, 109 may be the same or different. Suitable hydrogenation catalysts may be selected based on the expected operating conditions, which may vary between the column 70 and the side reactors 100, 106.

Figure 9:
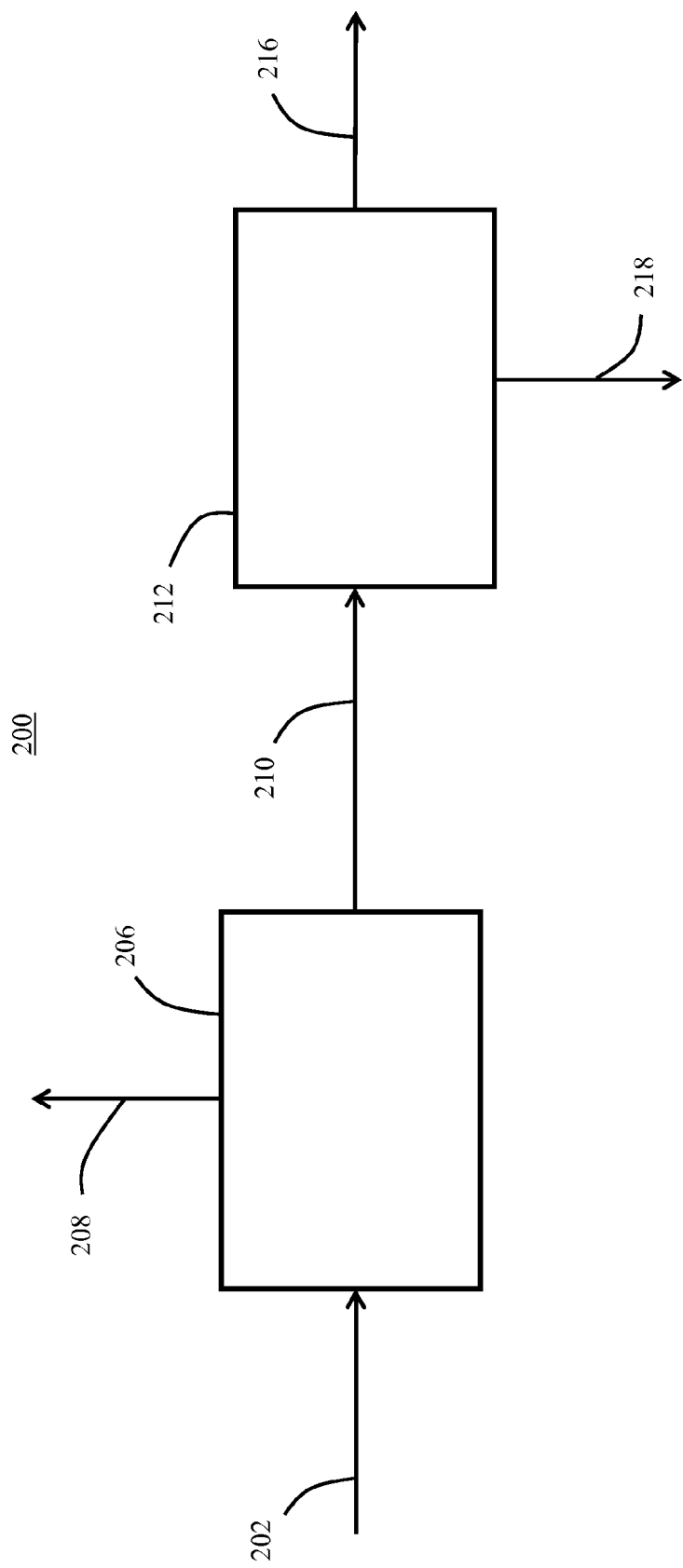
FIG. 9 illustrates a schematic flow diagram of a reactive distillation system with a recycle according to an embodiment.

As schematically illustrated in FIG. 9, an ethyl acetate production system 200 may comprise a products separation and/or purification section 212 for use in removing a portion of any byproducts or impurities from the product stream. In some embodiments, the ethyl acetate product stream produced in the processes and systems described herein may comprise one or more impurities. In some embodiments, the ethyl acetate product stream produced in the reactive distillation systems described with respect to FIG. 3-8 may comprise less than about 10 wt. %, less than about 8 wt. %, less than about 6 wt. %, less than about 4 wt. %, less than about 2 wt. %, or less than about 1.5 wt. % impurities, and in some embodiments, more than about 0.01 wt. %, more than about 0.1 wt. %, more than about 0.5 wt. %, or more than about 1 wt. %. The products separation section 212 may be configured to provide at least one product stream 216 comprising ethyl acetate having a purity of greater than about 90%, greater than about 95%, greater than about 96%, greater than about 97%, greater than about 98%, greater than about 99%, or greater than about 99.5% ethyl acetate by weight. At least one additional stream 218 may be produced comprising the remaining components of the product stream 210 from the ethyl acetate production process 206 (e.g., a reactive distillation column as described above). In an embodiment, a plurality of streams can be produced in the separation section comprising a stream 216 predominantly comprising ethyl acetate, and a stream 218 predominantly comprising the impurities removed from the ethyl acetate. In some embodiments, the product stream 216 may undergo further processing to remove one or more impurities. For example, an optional dehydration process may be carried out to remove any water present in the product stream 216.

As schematically illustrated in FIG. 9, a system 200 for producing ethyl acetate may comprise a feed stream 202 comprising ethanol that can be fed to the reactive distillation system 206. In an embodiment, the reactive distillation system 206 may comprise any of the reactive distillation systems described with respect to FIG. 3-8 herein. The reactive distillation system may produce an overhead product stream 208 and a bottoms product stream 210. The overhead product stream 208 may comprise hydrogen along with trace amounts of other light components (e.g., ethanol, etc.) and may generally correspond to any of the streams 19, 59, and/or 88 as illustrated in FIGS. 3-8. Similarly, the bottoms product stream 210 may comprise ethyl acetate, at least a portion of any unreacted ethanol, and/or additional reaction products (e.g., byproducts, impurities, etc.), and the bottoms product stream 210 may generally correspond to any of the streams 22, 36, 58, and/or 92 as illustrated in FIGS. 3-8.

A products separation section 212 may receive the bottoms product stream 210 from the reactive distillation system 206. The products separation section 212 may comprise any number or type of separation units, which may employ pressure- or temperature-swing distillation, pressure- or temperature-swing adsorption, membrane-based separation, cryogenic distillation, extraction, and/or any other suitable separation technology, all of which may be used to generate a desired product distribution. The products separation section 212 may generally produce an ethyl acetate product stream 216. The ethyl acetate product stream 216 may comprise ethyl acetate having a purity of greater than about 90%, greater than about 95%, greater than about 96%, greater than about 97%, greater than about 98%, greater than about 99%, or greater than about 99.5% ethyl acetate by weight. In addition to the ethyl acetate product stream 216, one or more additional streams may be produced by the products separation section 212. In an embodiment, an impurities stream 218 may be produced. The impurities stream 218 may comprise one or more reaction products (e.g., butanol, one or more aldehydes and/or ketones, etc.). Each of the potential product streams 216, 218 may exit the system as separate product streams and/or exit the system 200 for use as fuel and/or as a feed to additional downstream processes. While illustrated as separate streams 216, 218 one or more of these streams may exit the system 200 as a combined product stream.

Figure 10:
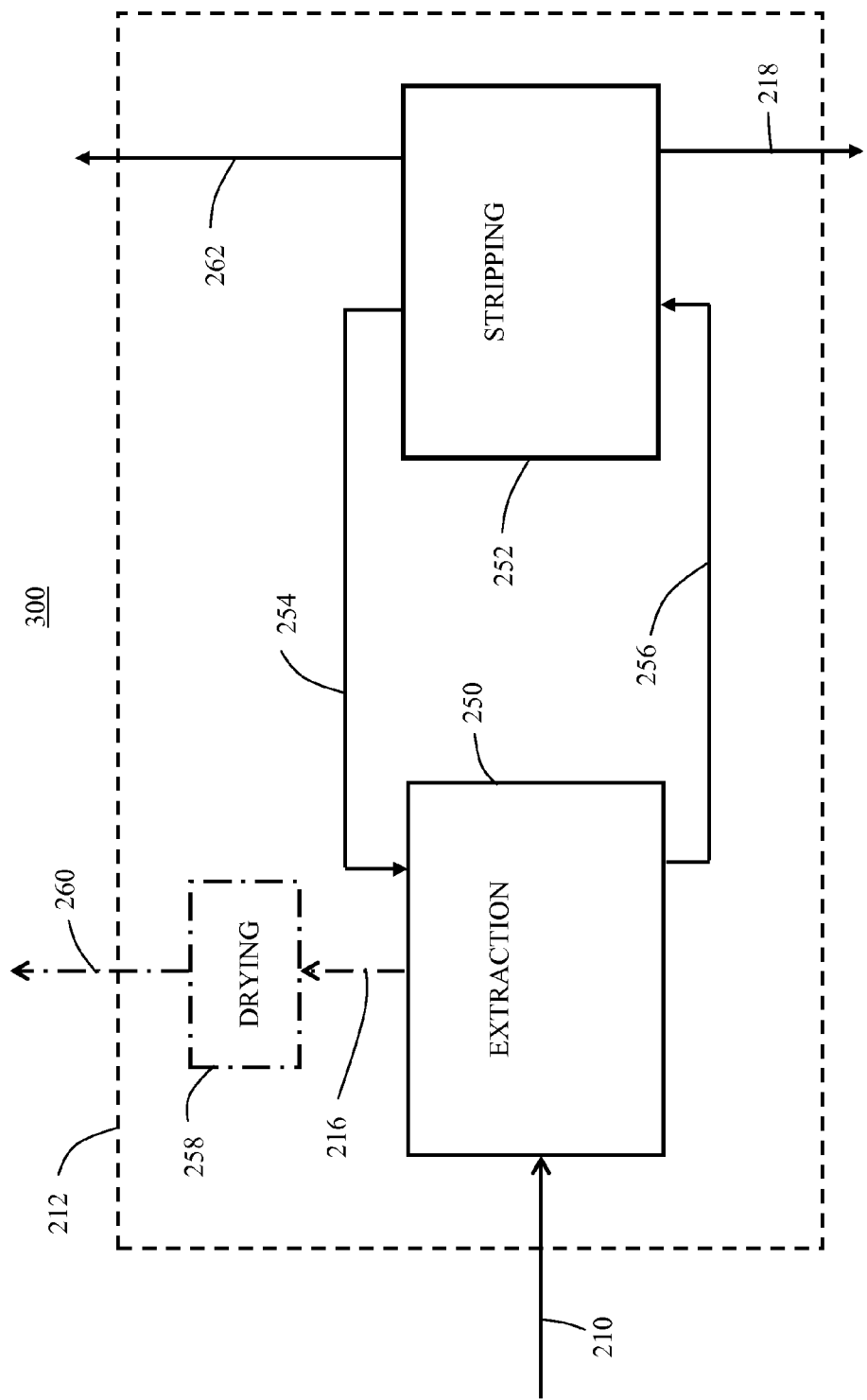
FIG. 10 illustrates a schematic flow diagram of a product separation system according to an embodiment.

In an embodiment as shown in FIG. 10, the separation section 212 may comprise an extraction process 300 for removing a portion of the impurities in the product stream 210. For example, an extraction process 300 may be used to separate at least a portion of one or more byproducts from the ethyl acetate in the product stream 210, thereby improving the quality and value of the ethyl acetate product stream. In this embodiment, the separation section 212 used to carry out the extraction process 300 may be the same or similar to the separation section described above with respect to FIG. 9. The extraction process 300 generally comprises an extraction section 250 in which the product stream 210 is contacted with a solvent in a solvent stream 254 to transfer or remove at least a portion of the impurities from the product. The extract stream 256 comprising the impurities transferred from the product can then be regenerated in a stripping section 252, which generally involves separating the impurities from the solvent to allow the impurities to be removed from the system and the solvent to be recycled.

The extraction process 300 may receive the bottoms product stream 210 from a reactive distillation system, which may comprise any of the reactive distillation systems described with respect to FIG. 3-8 herein. The extraction process 300 may comprise the extraction section 250 in which the bottoms product stream 210 is contacted with a solvent in a solvent stream 254. In an embodiment, the extraction section 250 comprises a liquid-liquid contact vessel suitable for contacting two liquid streams. Suitable vessels and extraction section 250 configurations are described in more detail herein. The solvent may draw a portion of one or more impurities from the bottoms product stream 210 into the solvent phase. The bottoms product stream 210 having the portion of the impurities removed may then exit the extraction section 250 as a purified product stream 216. The extract comprising the solvent and the portion of the impurity compound transferred from the bottoms product stream 210 may then exit the extraction section 250 as an extract stream 256.

An optional drying section 258 may serve to remove any remaining solvent or a component of a solvent (e.g., water from an aqueous solvent) from the purified product stream 216. The resulting dried purified product stream 260 may then leave the system as the final product stream. Any suitable drying units may be used to remove at least a portion of the solvent from the purified product stream 216. Suitable drying units may include, but are not limited to, industrial dehydration units comprising adsorbents such as Zeolites, alumina, silica, and other drying agents arranged in a pressure and/or temperature swing configuration, and/or liquid absorption (e.g., liquid-liquid extraction, gas-liquid extraction, etc.) using a drying agent. The purified product stream 216 and/or the dried purified product stream 260 may comprise ethyl acetate having a purity of greater than about 90%, greater than about 95%, greater than about 96%, greater than about 97%, greater than about 98%, greater than about 99%, or greater than about 99.5% ethyl acetate by weight.

In order to separate the impurities from the solvent, the extract stream 256 may be transferred to a stripping section 252. In an embodiment, the impurities may be removed using vapor-liquid stripping, heating, liquid-liquid phase separation, flashing and/or distillation, and/or any other suitable technique. Suitable vessels and stripping section 252 configurations are described in more detail herein. As shown in FIG. 10, the stripping section 252 may result in the separation of the impurities from the extract stream 256, thereby producing a liquid impurities stream 218 and/or a vapor impurities stream 262, and a regenerate solvent stream 254. In some embodiments, different components of the impurities may leave the separation section 212 as either a vapor or a liquid, including those generated by the solvent and/or any reactions within the separation section 212. The solvent may be regenerated by removing at least a portion of the impurities in the stripping section 252. In some embodiments, only a portion of any extracted impurities can be removed in the stripping section 252, and the resulting regenerated solvent stream 254 may comprise a minor amount of impurities. The regenerated solvent stream 254 may be recycled to the extraction section 250 to serve as the solvent. In some embodiments, a new solvent stream (e.g., a makeup solvent stream) may enter the extraction section separately or with the regenerated solvent stream 254 to serve as the solvent in the extraction section 250. The liquid impurities stream 218 and/or vapor impurities stream 262 may exit the system for various downstream uses. In an embodiment, the impurities stream may comprise commercially valuable chemicals that can be transferred for sale. In some embodiments, the impurities may be further separated before being sold, or alternatively, the impurities can be used as fuel or any other suitable use.

When used with the ethyl acetate production systems and processes describe herein, the solvent used in the extraction process 300 may be selected to remove the expected impurities within the ethyl acetate product stream (e.g., bottoms product stream 210). As noted above, the synthesis of ethyl acetate by consecutive dehydrogenation and condensation of ethanol to ethyl acetate is accompanied by the formation of relatively small amounts of byproducts. At least a portion of the byproducts comprising various aldehydes, ketones, and the like can be removed to improve the quality and purity of the ethyl acetate. In an embodiment, the extraction process 300 can be used to selectively extract at least a portion of the byproducts that may be present in the ethyl acetate. In an embodiment, the solvent may be configured to selectively react with and extract the impurities in the ethyl acetate. For example, the solvent may comprise one or compounds configured to reversibly react with the impurities, thereby allowing the reaction to remove the impurities from the ethyl acetate in the extraction section 250 and then be reversed to release the impurities in the stripping section 252.

In an embodiment, the solvent may comprise a fluid comprising one or more extracting agents. In an embodiment, the extracting agent may comprise a nucleophilic compound that can react with aldehydes and/or ketones to form a corresponding adduct. The resulting reaction products may have an increased solubility in the aqueous fluid, thereby allowing the adducts to leave the ethyl acetate product stream 210 and enter the solvent stream 254 to form the extract stream 256. Within the stripping section 252, the adduct equilibrium may be shifted to release the extracting agents from the impurities. The impurities may then be separated from the solvent comprising the extracting agents using any suitable separation technique such as vaporization and/or liquid-liquid separation.

Various extracting agents can be used in the aqueous solvent. In an embodiment, the extracting agents can comprise sulfur and/or nitrogen. Suitable extracting agents can include, but are not limited to, hydrazine ($N_2H_4$), hydroxylamine ($NH_2OH$), semicarbazide ($H_2NNH(C=O)NH_2$), phenylhydrazine ($C_6H_5N_2H_3$), phenylhydroxylamine ($C_6H_5NHOH$), sodium hydrogen sulfite ($NaHSO_3$/$Na_2S_2O_5$), sodium sulfite ($Na_2SO_3$), salts thereof, aqueous solutions thereof, and any combinations thereof. While any of these extracting agents can be used, reference will be made to sodium hydrogen sulfite in the following discussion as an example.

In an embodiment, an aqueous solution of sodium hydrogen sulfite (which can also be referred to as sodium bisulfite) can be used as the solvent in the extraction process 300. Sodium hydrogen sulfite can be sourced as a solid, which usually comprises a mixture of $NaHSO_3$ and $Na_2S_2O_5$. An aqueous solution can be made from the salt, and the use of an aqueous solution of sodium hydrogen sulfite provides an inexpensive, low toxicity solution that can serve as the solvent in the extraction process. Additional extracting agents can include sodium sulfite ($Na_2SO_3$). Sodium sulfite can be used by directly dissolving sodium sulfite in a solvent, or sodium hydroxide (NaOH) can be added to sodium hydrogen sulfite as a solid or in solution. Further a mixture of sodium hydrogen sulfite and sodium sulfite can be used in an ratio. The reactive moiety in the aqueous solution of sodium hydrogen sulfite is the hydrosulfite ion ($HSO_3^-/S_2O_5^{2-}$) and reactive moiety in an aqueous solution of sodium sulfite is the sulfite ion ($SO_3^{2-}$). Thus any soluble hydrosulfite and/or sulfite compound can also be used in similar manner regardless of the counter ion. For example hydrosulfite compounds including $K^+$, $NH_4^+$ salts can also be used along with or in place of sodium hydrogen sulfite.

The aqueous solution comprising the hydrosulfite ion reacts reversibly with aldehydes and ketones such as 2-butanone, acetone, acetaldehyde, thereby rendering them more water soluble as sodium salts of hydrosulfite adducts of the corresponding compounds. For example, the following reaction may take place when the aqueous solution comprising the hydrosulfite ion is contacted with a fluid comprising a ketone (e.g., 2-butanone) as follows:

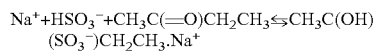

The resulting sodium salt of the 2-butanone sulfonate adduct has higher solubility in water compared to ethyl acetate thus leading to partial extraction of 2-butanone from the organic (ethyl acetate) phase, thereby increasing the ethyl acetate phase purity. The resulting adduct may be formed by various aldehydes and/or ketones, thereby providing for the ability to selectively improve the removal efficiency of the impurities generated in the ethyl acetate production process during the extraction section 250.

Within the extraction process 300, various factors may affect the extraction efficiency of the solvent within the extraction section 250 including the concentration of the extracting agent in the solvent, the ratio of the solvent to the ethyl acetate product, and the temperature at which the extraction takes place. With respect to the concentration of the extracting agent in the solvent, there are several considerations that can have an affect on the concentration of the compound in the solvent. In general, a higher concentration of the extracting agent (e.g., $NaHSO_3$) in the aqueous fluid can reduces the ethyl acetate solubility in the solution. However, as the concentration of the extracting agent rises above a certain amount, the resulting adduct may precipitate out of solution. Such precipitation may complicate a continuous process in terms of solids handling equipment. In general, the amount of the extracting agent in the aqueous fluid should be sufficient to provide an excess of the ions in solution but less than an amount that would result in precipitation of the resulting adduct in the extract, which indicates that the solubility limit of the adduct has been reached. Thus, the concentration of the extracting agent in the solvent may vary based on the concentration of the impurities in the ethyl acetate product stream. In an embodiment, the concentration of the extracting agent (e.g., sodium hydrogen sulfite) in the aqueous solution can vary. In an embodiment, the extracting agent can comprise sodium hydrogen sulfite, and the amount of sodium hydrogen sulfite in the aqueous solution can vary and may generally range from about 50 grams to about 420 grams, from about 300 grams to about 420 grams of solid (e.g., a mixture of $NaHSO_3$ and $Na_2S_2O_5$) per liter of water. When the extracting agent is sodium hydrogen sulfite, the concentration may generally range from about 5 to about 42 grams per 100 milliliters of solution, or from about 30 to about 42 grams per 100 milliliters of solution at about 68° F. (about 20° C.). In an embodiment, the extracting agent may be provided in the form of sodium sulfite and/or a hydrate thereof, and the concentration may generally range from about 5 to about 68 grams per 100 milliliters of solution when the sodium sulfite is provided as sodium sulfite heptahydrate. The concentration of the extracting agent may vary based on the composition of the extracting agent, the form in which it is provided, the temperature of the solution, the composition of the solution, and the like.

With respect to the temperature at which the extraction process takes place, it has been discovered that the extraction efficiency of the impurities in the ethyl acetate with the aqueous solvent generally increases at a lower temperature relative to a higher temperature extraction. Accordingly, lowering the temperature of the extraction process may result in a greater amount of the impurities being transferred from the ethyl acetate product to the solvent stream. In general, the extraction section 250 may operate within a temperature of between about 10° C. to about 70° C., from about 15° C. to about 60° C., or from about 20° C. to about 50° C.

Once the aqueous solvent contacts the ethyl acetate product stream (e.g., bottoms product stream 210) in the extraction step 250, the aqueous fluid comprising the adducts can be separated from the organic ethyl acetate phase using liquid-liquid separation. The separated extract stream 256 can then be used to perform an additional extraction of impurities from an ethyl acetate product stream and/or the extract can be transferred to the stripping section 252 for regeneration. In general, the extract stream 256 comprising the adducts can be treated in the stripping section 252 to separate the organic compounds (e.g., the impurities, any dissolved ethyl acetate, etc.) from the aqueous solvent comprising the extracting agent. For example, the extract stream may be heated to reverse the adduct formation, and the organic phase can then be separated from the aqueous solution. In some embodiments, the adducts may be separated by crystallization followed by a subsequent treatment of the precipitated solids.

When the adducts remains dissolved in the aqueous fluid, the adducts can be decomposed by heating to reverse the equilibrium and release the impurities (e.g., the aldehydes/ketones) while regenerating the aqueous solution comprising the extracting agent for reuse. The impurities can then be separated using evaporation, distillation, and/or liquid-liquid phase separation. In an embodiment, the aqueous solution (e.g., the extract stream 256) may comprise the excess of sodium hydrogen sulfite, the dissolved sodium hydrogen sulfite adducts, and some amount dissolved ethyl acetate. The solution can be regenerated by heating the solution to a temperature suitable to reverse the adduct formation equilibrium. In an embodiment in which the nucleophile compound comprises sodium hydrogen sulfite, the regeneration can be achieved by heating the solution to a temperature between about 45° C. and about 100° C. At this temperature, the sodium hydrogen sulfite adduct decomposes to release the impurities and the $NaHSO_3$. The released impurities and any dissolved ethyl acetate can be separated from the aqueous solution and collected. In some embodiments, the organic compounds can be vaporized (e.g., in a flash tank) or distilled from the aqueous solution, and/or alternatively the organic compounds can be separated based on a liquid-liquid phase separation. The remaining aqueous solution may comprise the regenerated solvent for use in the extraction process 300. In an embodiment, the separation process within the stripping section 252 may result in some minor amount of the organic compounds remaining in the aqueous solvent.

During the heating process some amount of the extracting agent may decompose to form an additional impurity. For example, when the extracting agent comprises sodium hydrogen sulfite, heating may result in some sulfur dioxide being lost due to decomposition. The decomposition products can be captured using an aqueous $NaHSO_3$ solution or an aqueous caustic solution (e.g., NaOH), which may be advantageous in preventing the release of the decomposition products to the atmosphere. The regenerated solvent solution in the stream 354 may have higher or lower extracting agent concentration than desired. The concentration may be adjusted through the addition of water, solid extracting agent, or an extracting agent solution until the desired concentration is reached.

In some embodiments, the adducts can be removed from the extract stream 256 by crystallization. For example, the adducts can be separated from the extract stream 256 by forming a sodium ketone/aldehyde hydrosulfite adduct crystals. If the adducts are crystallized out of solution, the resulting crystals can be separated physically. The crystals can then be heated to reverse the adduct formation. In an embodiment, the crystals may be dissolved in an aqueous solution prior to heating to reverse the adduct formation. The resulting organic impurities can then be separated from the extracting agent and any aqueous solution.

The extraction process can be carried out using various configurations and designs. An embodiment of an extraction process 350 is schematically illustrated in FIG. 11. In this embodiment, a product stream 310 is fed to the extraction section 302. The product stream may generally correspond to any of the streams 22, 36, 58, and/or 92 as illustrated in FIGS. 3-8. The product stream 310 may predominantly comprise ethyl acetate, though various byproducts including ketones and/or aldehydes such as 2-butanone, acetone, and/or acetaldehyde may also be present.

The extraction section 302 may also receive a solvent stream 319. In an embodiment, the solvent stream 319 may comprise an aqueous fluid and an extracting agent as described above. The solvent comprising the extracting agent may comprise an aqueous solution of hydrazine ($N_2H_4$), hydroxylamine ($NH_2OH$), semicarbazide ($H_2NNH(C=O)NH_2$), phenylhydrazine ($C_6H_5N_2H_3$), phenylhydroxylamine ($C_6H_5NHOH$), sodium hydrogen sulfite ($NaHSO_3$/$Na_2S_2O_5$), sodium sulfite ($Na_2SO_3$), salts thereof, aqueous solutions thereof, and any combination thereof. Additional solvents useful with the extraction process can include dichloromethane-ethanol and methyl isobutyl ketone (MIBK). The extraction section 302 may comprise one or more liquid-liquid contact devices configured to contact the two liquid streams 319, 310. Various liquid-liquid contact devices can be used including an extraction column, which may comprise packing material (e.g., structured packing, random packing, trays, etc.) configured to increase mixing and the available contact area for mass transfer between the two liquids. Additional suitable structures can include a series of mixer settlers, sieve trays, a Kerr-McGee extractor, a packed tower, a rotating disk contactor, a Scheibel extractor, a pulsed column, and a centrifugal extractor. The extraction may be carried out in a co-current, counter-current, and/or cross-current flow scheme, each of which is described in more detail below with respect to FIGS. 13, 14, and 15, respectively. In an embodiment, the extraction section can comprises a counter-current flow arrangement between the solvent and product streams.

A contact device within the extraction section may comprise a number of stages configured to provide the degree of impurity removal from the product stream 310 and/or a desired purity of the purified ethyl acetate product stream. In an embodiment, the contact device, or a plurality of contact devices, can contain between about 1 to about 100 stages, or between about 1 to about 50 stages. The contact device or contact devices may operate at any suitable pressure. In an embodiment, the contact device may operate at a pressure ranging from about 1 atm to about 80 atm, and a temperature of between about 10° C. to about 70° C., from about 15° C. to about 60° C., or from about 20° C. to about 50° C.

Within the extraction section 302, at least a portion of the impurities may be transferred to the solvent. In an embodiment, the extracting agent may react with a portion of the impurities in the product stream 310 to form an adduct and improve the solubility of the impurity in the solvent phase. Once the product stream 310 and the solvent stream 319 have been contacted and separated within the extraction section 302, a purified product stream 216 and an extract stream 256 may exit the extraction section 302. The purified product stream 216 may have an increased purity of ethyl acetate relative to the entering product stream 310. As described above, the purified product stream 216 may pass to a drying unit to further remove any solvent to further purify the purified product stream. In an embodiment, the purified product stream 216 and/or a dried, purified product stream may comprise ethyl acetate having a purity of greater than about 90%, greater than about 95%, greater than about 96%, greater than about 97%, greater than about 98%, greater than about 99%, or greater than about 99.5% ethyl acetate by weight.

The extract stream 256 may comprise the solvent and the impurities removed from the product stream 310. The extract stream 256 may pass to the stripping section 304. In an embodiment, the extract stream 256 may comprise a solvent fluid, the adducts formed by the reaction between the extracting agent and the impurities, any excess extracting agent, and potentially some amount of dissolved ethyl acetate. The stripping section 304 may comprise one or more separation devices configured to separate the impurities from the solvent and any extracting agent. Various separation devices can be used including phase separators and liquid-liquid separators. In an embodiment, the separation device within the stripping section 304 may comprise a flash tank. In this embodiment, the extract stream 256 may enter the flash tank, be heated to a temperature sufficient to dissociate the adduct, and evaporate at least a portion of any impurities and dissolved ethyl acetate. The flash tank may operate at a pressure ranging from about 1 atm to about 80 atm, and a temperature of between about 70° C. to about 120° C., or from about 85° C. to about 100° C. In some embodiments, the separation device may comprise a distillation column. The extract stream 256 can be heated within the distillation column to dissociate the adducts into the impurities and the extracting agent within the solvent. The impurities may then be separated by distillation. The distillation column may comprise about 1 to about 100 stages, or about 1 to about 50 stages. The distillation column may operate at a pressure ranging from about 1 atm to about 80 atm. The temperature and pressure may be selected based on the equilibrium on each stage within the distillation column. In an embodiment, the temperature within the column may range from about 50° C. to about 200° C., or from about 70° C. to about 150° C.

In an embodiment, the stripping section may operate at a vacuum pressure relative to atmospheric pressure. A lower operating pressure is generally expected to reduce the temperature at which the solvent can be separated from the impurities when the adducts are dissociated. In an embodiment, the stripping section may operate at a pressure ranging from about 0.001 atm to about 1 atm and at a temperature of between about 45° C. and about 100° C. In general, the solvent and/or extracting agent may break down during the heating process in the stripping section, potentially releasing contaminants into the vapor stream. By operating at a reduced pressure, and resulting reduced temperature, the rate of solvent and/or extracting agent loss may be reduced. For example, by lowering the temperature at which the stripping occurs, the rate at which any hydrosulfite/sulfite in solution breaks down to form sulfur dioxide can be reduced or limited.

When the stripping section 304 comprises a phase separator, an overhead product stream 306 may exit the stripping section 304 and pass to a condenser 308. The overhead stream 306 may comprise the separated impurities, dissolved ethyl acetate, and potentially minor amount of water and decomposition products resulting from a breakdown of the extracting agent. Within the condenser 308, the temperature of the overhead stream 306 may be reduced to condense the impurities into a liquid, which may leave the condenser 308 as an impurities stream 312. The impurities stream 312 may exit the system for sale, for use as fuel, and/or as a feed to one or more suitable downstream processes. Any remaining gases may exit the condenser as an off-gas stream 310. The off-gas stream 310 may comprise a portion of the vaporized impurities, ethyl acetate, and any decomposition products from the solvent. The off-gas stream 310 can be vented to the atmosphere or a flare, or as shown in FIG. 11, recycled to be combined with the regenerated solvent stream 307. The regenerated solvent stream 307 may leave the stripping section 304 as a bottoms stream and pass to the contactor 314. The off-gas stream 310 may then be re-absorbed within the contactor 314. The combined regenerated solvent stream 254 may pass to a heat exchanger 316, which may comprise any of the types of heat exchangers described herein. The regenerated solvent stream 254 may be cooled within the heat exchanger 316 to a temperature suitable to allow the extracting agent within the solvent to form an adducts with any corresponding impurities in the product stream 310. The cooled, regenerated solvent stream 254 may then be combined with an optional solvent make-up stream 318 to form the solvent stream 319. The make-up stream may include the solvent comprising the extracting agent in any suitable concentration. In an embodiment, the make-up stream may server to adjust the concentration of the extracting agent within the solvent stream 319 to a desired level.

In some embodiments, the stripping section 304 may comprise a liquid-liquid separator. The liquid-liquid separator may operate at a pressure ranging from about 1 atm to about 80 atm. The extract stream 256 may be heated to a temperature in the range of between about 40° C. to about 120° C., or from about 45° C. to about 100° C. within the separator, which may be sufficient to dissociate the adduct. The impurities may then form an organic liquid phase that is at least partially insoluble in the aqueous solvent. The resulting phases may be separated in a liquid-liquid phase separation device, such as a settling tank or settling tower. Suitable draw points may be used to provide a regenerated solvent stream 307 and an organics stream 306. The organics stream 306 may leave the system without any further separation or processing. The liquid-liquid separator may comprise a gas vent suitable for passing any off-gases back to the contactor 314. The aqueous phase may leave the liquid-liquid separator as the regenerated solvent stream 307 and pass back to the extractor through the contactor 314 and heat exchanger 316 as described above.

FIG. 12 illustrates an embodiment of a stripping section 354 that is similar to the stripping section 304 described with respect to FIG. 11. In the interest of clarity, similar components will not be described. The stripping section 354 may comprise any of the separation devices operating at any of the operating conditions as described above with respect to FIG. 11, and the stripping section 354 can be used with the remaining components of the extraction process 350 illustrated in FIG. 11. The stripping section 354 differs from the stripping section 304 of FIG. 11 in that a purge gas stream 364 can be introduced into the stripping section 354, which can aid in the extraction of the impurities from the solvent solution. In an embodiment, the purge gas can comprise a gas having a boiling point significantly below that of the impurities, and the purge gas may have a low solubility in the solvent and/or impurities to aid in separation from the solvent and impurities. The purge gas can include, but is not limited to, nitrogen, oxygen, argon, helium, hydrogen, carbon dioxide, and any combination thereof (e.g., air). The use of the purge gas may aid in removing the impurities from the extract stream 256 while maintaining a relatively low stripping temperature. The use of the low temperature may aid in limiting or reducing the breakdown of the solvent and/or extracting agent, which can potentially resulting the generation of pollutants.

The extract stream 256 can be introduced into the stripping section 354 and can include a solvent fluid, the adducts formed by the reaction between the extracting agent and the impurities, any excess extracting agent, and potentially some amount of dissolved ethyl acetate. As the liquid extract stream 256 flows through the stripping section, a purge gas stream 364 can be introduced into the lower portion of the stripping section 354. The ratio of the purge gas volumetric flow rate to the extract stream volumetric flowrate can range from about 1,000:1 to about 1:100, and the ratio may be based on the amount of impurities present in the extract stream, the conditions within the stripping section 354, and/or the solubility of the impurities in the purge gas. The extract stream 256 can be heated to a temperature in the range of about 45° C. to about 100° C. before and/or within the stripping section 354, resulting in at least a partial dissociation of the adducts. Vapor-liquid stripping can then take place between the impurities released from the adducts and the purge gas. Since the impurities would generally have a lower boiling point than the solvent, the impurities could expect to be stripped into the purge gas stream.

The stripping section 354 can have an overhead product stream 356 that can pass to a cooler 358 and into a separator 360. The overhead stream 356 may comprise the purge gas, impurities stripped by the purge gas, and potentially minor amount of solvent, ethyl acetate, and decomposition products resulting from a breakdown of the extracting agent. Within the cooler 358, the temperature of the overhead stream 356 may be reduced to condense the impurities into a liquid, which may then pass to the separator 360 and leave as an impurities stream 362. The impurities stream 362 may exit the system for sale, for use as fuel, and/or as a feed to one or more suitable downstream processes. The purge gas may not condense and may pass out of the separator 360 as the purge gas stream 364 for recycle to the stripping section 354. The purge gas stream 364 may comprise a minor amount of the impurities, the solvent, and the decomposition products, that can reach an equilibrium in the process due to the recycling of the purge gas stream 364. The regenerated solvent stream 307 can be processed and/or recycled as described with respect to the regenerated solvent stream in FIG. 11.

The extraction section may comprise a number of flow configurations. The extraction may be carried out in a co-current, counter-current, and/or cross-current flow scheme, as schematically illustrated in FIGS. 13, 14, and 15, respectively. An embodiment of a co-current extraction scheme is illustrated in FIG. 13. In this embodiment, the extraction section may comprise a plurality of stages 402, 404, 406. For each stage 402, 404, 406, the product stream 310 and the solvent stream 319 may enter the stage and flow together through the stage. The solvent and product may be separated within the stage, for example using a settler/phase separator. Each phase may then pass to the next stage as separate phases. Alternatively, the combined fluids may pass to the next stage as a single stream. In general, the co-current flow of solvent and product may allow the two streams to reach an equilibrium, and therefore, the co-current flow may only provide an extraction equivalent to a single theoretical stage. However, additional stages may be useful in practice to provide additional residence/contact time to approach the equilibrium concentrations and mass transfer of the impurities from the ethyl acetate product into the solvent phase. The solvent phase may be separated from the product phase within the last stage or within a separator downstream of the last stage to produce the extract stream 256 and the purified product stream 216. While illustrated as separate stages 402, 404, 406, the stages may be present in a single physical vessel. Further, while three stages 402, 404, 406 are shown in FIG. 13, less than three stage or more than three stages may be used. In an embodiment, the number of stages may be between about 1 and about 50 stages.

An embodiment of a counter-current extraction scheme is illustrated in FIG. 14. In this embodiment, the extraction section may comprise a plurality of stages 408, 410, 412. The product stream 310 may enter at a first of the stages and the solvent stream 319 may enter the last stage and flow countercurrently through each stage. The phases may be arranged to allow the phases to flow countercurrently based on density differences, with the organic product phase flow upwards and the aqueous solvent phase flow downwards. The countercurrent flow of the product and solvent may result in the most efficient extraction and mass transfer of the three flow schemes. The solvent phase may be separated from the product phase within the first stage 408 to allow the extract stream 256 to leave the extraction section 302. Similarly, the product phase may be separated from the solvent phase within the last stage 412 to allow the purified product stream 216 to leave the extraction section 302. While illustrated as separate stages 408, 410, 412, the stages may be present in a single physical vessel. Further, while three stages 408, 410, 412 are shown in FIG. 14, less than three stage or more than three stages may be used. In an embodiment, the number of stages may be between about 1 and about 50 stages.

An embodiment of a cross-current extraction scheme is illustrated in FIG. 15. In this embodiment, the extraction section may comprise a plurality of stages 414, 416, 418. The product stream 310 may enter at a first of the stages and progress through each stage 414, 416, 418. The solvent stream 319 can be divided into portions 420, 422, 424, which may have the same or different flow rate. The portions 420, 422, 424 may pass to each stage 414, 416, 418, respectively, to contact the product within each stage 414, 416, 418. Within each stage 414, 416, 418, the solvent phase may be separated from the product phase, and the solvent phase portions may be recombined to form extract stream 256. The solvent phase may pass out of the last stage 418 as the purified product stream 216. The use of the cross-current flow configuration may allow the concentration of the impurities in the ethyl acetate product stream to be decreased in each stage. In an embodiment, the cross-current extraction scheme may comprise separate vessels (e.g., contactors, settlers, etc.) for each stage. In some embodiments, the stages may be present in a single physical vessel with internal contactors and separators. Further, while three stages 408, 410, 412 are shown in FIG. 15, less than three stage or more than three stages may be used. In an embodiment, the number of stages may be between about 1 and about 50 stages.

While described separately, the extraction section 302 may comprise any combination of the extraction schemes illustrated in FIGS. 13, 14, and 15. For example, each stage of the cross-current flow scheme may comprise a co-current or counter-current individual flow scheme. Various other combinations may also be possible.

Dehydrogenation and Dimerization Catalysts

Suitable dehydrogenation and dimerization catalysts are capable of converting at least a portion of the alcohol (e.g., ethanol) in a feed stream to a higher valued product such as ethyl acetate. Any catalyst capable of carrying out a dehydrogenation and dimerization reaction may be used alone or in combination with additional catalytic materials in the reactors. In an embodiment, suitable dehydrogenation and dimerization catalysts can generally comprise metals and/or oxides of copper, barium, ruthenium, rhodium, platinum, palladium, rhenium, silver, cadmium, zinc, zirconium, gold, thallium, magnesium, manganese, aluminum, chromium, nickel, iron, molybdenum, sodium, strontium, tin, and mixtures thereof. In many cases, the catalyst material will be provided on a support material. The catalyst can be treated with a carbonate (e.g., sodium carbonate), reduced with hydrogen, and/or other suitable treatments prior to use.

In certain embodiments, the dehydrogenation and dimerization catalyst may include a catalyst support. The catalyst support stabilizes and supports the catalyst. The type of catalyst support used depends on the chosen catalyst and the reaction conditions. Suitable supports may include, but are not limited to, carbon, silica, silica-alumina, alumina, zirconia, titania, ceria, vanadia, nitride, boron nitride, heteropolyacids, hydroxyapatite, zinc oxide, chromia, zeolites, carbon nanotubes, carbon fullerenes, and any combination thereof.

The dehydrogenation and dimerization catalyst can be employed in any of the conventional types or structures known to the art. It may be employed in the form of extrudates, pills, pellets, granules, broken fragments, or various special shapes. In an embodiment, consideration of the use of the catalyst in the reactive distillation system and/or as a mass transfer surface within the distillation column may be taken into account when determining a suitable shape. For example, the catalyst may have a shape similar to structured packing material or suitable for insertion in a structured packing. When the hydrogenation catalyst is used with one or more side reactors, the catalyst may be disposed within a reaction zone, and the feed may be passed therethrough in the liquid, vapor, or mixed phase, and in either upward or downward, or inward or outward flow.

The dehydrogenation and dimerization catalyst may typically have a range of metal loadings. In an embodiment, the catalyst may have a copper oxide weight loading (i.e., weight percentage) of between about 0.5% and about 90%, between about 10% and about 70%, between about 20% and about 65%, between about 30% and about 60%, or about 40% and about 50%. In an embodiment, the catalyst may have a zinc oxide weight loading of between about 20% and about 60%, between about 30% and about 50%, or between about 40% and about 50%. In an embodiment, the catalyst may have a chromium oxide weight loading of between about 20% and about 60%, or between about 30% and about 50%.

In an embodiment, the catalyst may comprise $CuO/ZnO/Al_2O_3$. In this embodiment, the catalyst may have a copper oxide weight loading of between about 0.5% and about 90%, between about 10% and about 70%, between about 20% and about 65%, between about 30% and about 60%, or about 40% and about 50%, and the zinc oxide and alumina may comprise the balance of the weight. In an embodiment, the catalyst may comprise $CuO/ZnO/ZrO_2/Al_2O_3$, and the catalyst may have a copper oxide weight loading of between about 40% to about 90%, with the remainder of the components forming the balance of the catalyst weight. In an embodiment, the catalyst may comprise $CuO/ZnO/ZrO_2/Cr_2O_3$, and the catalyst may have a copper oxide weight loading of between about 20% to about 90% and a chromium oxide weight loading between about 30% and about 50%, with the remainder of the components forming the balance of the catalyst weight. In an embodiment, the catalyst may comprise $CuO/ZrO_2/Al_2O_3$. In an embodiment, the catalyst comprises an alkaline earth metal and/or alkaline earth metal oxide and copper and/or copper oxide on a support. In this embodiment, the support may comprise silica.

Any of the materials useful as hydrogenation and dimerization catalysts, may be synthesized using a variety of methods. In an embodiment, the dehydrogenation and dimerization catalyst may be prepared via wet impregnation of a catalyst support. Using the wet-impregnation technique, a metal nitrate dissolved in a suitable solvent may be used to prepare the catalyst, however any soluble compound would be suitable. A sufficient amount of solvent should be used to fully dissolve the metal nitrate and appropriately wet the support. In one embodiment, copper nitrate and ethanol and/or water may be mixed in an amount sufficient such that the copper nitrate dissolves. Additional metal nitrates may also be added to provide a catalyst with additional components. The solute may then be combined with a suitable support material of appropriate particle size. The mixture may then be refluxed at a temperature of approximately 100° C. for approximately several hours (e.g., three to five hours) and then allowed to dry at a temperature of about 110° C. The dried material may then be heated to 200° C. to remove the $NO_x$ component, and then the materials may be calcined at about 450° C. to about 550° C. at a heating rate of about one to ten ° C./min. The amount of metal nitrate used in the wet-impregnation technique can be adjusted to achieve a desired final metal weight loading of the catalyst support.

When multiple components are used to provide a catalyst disposed on a support, each component can be added via the wet-impregnation technique. The appropriate salts can be dissolved and impregnated on a support in a co-impregnation process or a sequential process. In a co-impregnation process, measured amount of the appropriate plurality of metal salts may be dissolved in a suitable solvent and used to wet the desired catalyst support. The impregnated support can then be dried and calcined to provide a final catalyst with a desired weight loading. In the sequential impregnation process, one or more measured amounts of salts may be dissolved in a suitable solvent and used to wet the desired catalyst support. The impregnated support can then be dried and calcined. The resulting material can then be wetted with one or more additional salts that are dissolved in a suitable solvent. The resulting material can then be dried and calcined again. This process may be repeated to provide a final catalyst material with a desired loading of each component. In an embodiment, a single metal may be added with each cycle. The order in which the metals are added in the sequential process can be varied. Various metal weight loadings may be achieved through the wet-impregnation technique. In an embodiment, the wet-impregnation technique may be used to provide a catalyst having a copper weight loading ranging from about 0.5% and about 50%, with one or more additional components having a weight loading between about 0.1% and about 10%.

The dehydrogenation and dimerization catalysts may also be prepared via a co-precipitation technique. In this technique, a measured amount of one or more appropriate metal nitrates (or other appropriate metal salts) are dissolved in de-ionized water. The total metal concentration can vary and may generally be between about 1 M and about 3 M. The metal-nitrate solution may then be precipitated through the drop-wise addition of the solution to a stirred, equal volume of a sodium hydroxide solution at room temperature. The sodium hydroxide solution may generally have a concentration of about 4M, though other concentrations may also be used as would be known to one of skill in the art with the benefit of this disclosure. After addition of the metal nitrate solution, the resulting suspension can be filtered and washed with de-ionized water. The filtered solids can be dried overnight, for example, at a temperature of about 110° C. The resulting mixed metal oxide can then be processed to a desired particle size. For example, the resulting mixed metal oxide can be pressed to a desired form, ground, and then sieved to recover a catalyst material with a particle size in a desired range. Catalysts prepared using the co-precipitation technique may have higher metal loadings than the catalysts prepared using the wet-impregnation technique.

The catalyst prepared via the co-precipitation technique may be used in the prepared form and/or a catalyst binder can be added to impart additional mechanical strength. In an embodiment, the prepared catalyst may be ground to a fine powder and then stirred into a colloidal suspension (e.g., a colloidal suspension of silica and/or alumina) in an aqueous solution. The resulting suspension may be stirred while being heated and allowed to evaporate to dryness. The heating may take place at about 80° C. to about 130° C. The resulting solid can then be processed to a desired particle size. For example, the resulting solid can be pressed to a desired form, ground, and then sieved to recover a catalyst material with a particle size in a desired range. Alternatively, the colloidal suspension may be added to the 4M sodium hydroxide precipitation solution prior to addition of the metal nitrate solution in the co-precipitation technique. Various metal weight loadings may be achieved through the co-precipitation technique. In an embodiment, the co-precipitation technique may be used to provide a catalyst having a copper weight loading ranging from about 2% and about 80%, with one or more additional components having a weight loading between about 2% and about 40%.

The resulting catalyst from either the wet-impregnation technique and/or the co-precipitation technique may be further treated prior to use in the reactive distillation system disclosed herein. In an embodiment, the catalyst may be treated with a sodium carbonate solution for a period of time to improve the selectivity of the catalyst. In this process, the catalyst may be soaked in an aqueous solution of sodium carbonate for a period of time ranging from about 1 hour to about 48 hours, or alternatively about 2 hours to about 24 hours. In an embodiment, the sodium carbonate solution may have a concentration of about 0.2 M. The catalyst may then be filtered and allowed to dry at about room temperature. In an embodiment, the sodium carbonate may comprise from about 0.2 to about 3.0 weight percent of the catalyst after being contacted with the sodium carbonate solution.

In another treatment process, the catalyst may be reduced with hydrogen prior to use. In this embodiment, the catalyst may be heated and contacted with hydrogen, which may be flowing over the catalyst, for a period of time sufficient to reduce the catalyst to a desired degree. In an embodiment, the catalyst may be contacted with hydrogen at a temperature of about 190° C. to about 240° C. The hydrogen treatment may be conducted in combination with the sodium carbonate treatment, and may be performed prior to and/or after the sodium carbonate treatment.

Without intending to be limited by theory, it is believed that the production of hydrogen during the dehydrogenation and dimerization reaction within the process may result in contact between the dehydrogenation and dimerization catalyst and a hydrogen stream sufficient to at least partially reduce the catalyst. Thus, the process described herein may have the potential for the in-situ reduction of the catalyst during use. This may result in an initial break-in period in which the catalyst conversion and selectivity may change before reaching a steady state conversion and selectivity. This in-situ reduction may be taken into account when considering the degree to which a catalyst should be pre-reduced with hydrogen.

In an embodiment, the dehydrogenation and dimerization catalyst described herein may be capable of achieving a relatively high conversion and/or selectivity of ethanol to ethyl acetate. As used herein, the "conversion" of ethanol to ethyl acetate refers to the amount of ethanol consumed in the conversion reaction as represented by the formula:

$$X_{ethanol} = 100 \left( \frac{F_{EtOH,0} - F_{EtOH}}{F_{EtOH,0}} \right)$$

where $F_{EtOH}$ represents the molar flow rates of ethanol in the reactor effluent (e.g., the product stream comprising the ethyl acetate), and $F_{EtOH,0}$ represents the molar flow rate of ethanol into the reactor inlet. As used herein, the "selectivity" of the conversion refers to the amount of ethanol that is consumed in the conversion reaction that is converted to ethyl acetate as represented by the formula:

$$S = 100 \left( \frac{2F_{EtOAc} + F_{AcH}}{F_{EtOH,0} - F_{EtOH}} \right)$$

where $F_{EtOAc}$ and $F_{AcH}$ represent the molar flow rate of ethyl acetate and acetaldehyde in the reactor effluent (e.g., the product stream comprising the ethyl acetate), respectively, and the remaining terms are the same as described above with respect to the conversion of ethanol. In an embodiment, the dehydrogenation and dimerization catalyst described herein may be capable of achieving a conversion of ethanol in the reactive distillation process described herein of at least about 10%, at least about 20%, at least about 30%, at least about 40%, or at least about 50%. In an embodiment, the dehydrogenation and dimerization catalyst described herein may be capable of achieving a selectivity of ethyl acetate in the reactive distillation process described herein of at least about 60%, at least about 70%, at least about 80%, at least about 85%, at least about 90%, at least about 95%, or at least about 96%.

Hydrogenation Catalysts

The hydrogenation catalyst generally can include a Group VIII metal and/or a Group VI metal. Examples of such a catalyst can include, but is not limited to, Cu, Re, Ni, Fe, Co, Ru, Pd, Rh, Pt, Os, Ir, and alloys or any combination thereof, either alone or with promoters such as W, Mo, Au, Ag, Cr, Zn, Mn, Sn, B, P, Bi, and alloys or any combination thereof. Other effective hydrogenation catalyst materials include either supported nickel or ruthenium modified with rhenium. In an embodiment, the hydrogenation catalyst also includes any one of the supports described below, depending on the desired functionality of the catalyst. The hydrogenation catalysts may be prepared by methods known to those of ordinary skill in the art.

In an embodiment, the hydrogenation catalyst includes a supported Group VIII metal catalyst and a metal sponge material (e.g., a sponge nickel catalyst). Raney nickel provides an example of an activated sponge nickel catalyst suitable for use in this invention. In an embodiment, the hydrogenation reaction in the invention is performed using a catalyst comprising a nickel-rhenium catalyst or a tungsten-modified nickel catalyst. One example of a suitable catalyst for the hydrogenation reaction of the invention is a carbon-supported nickel-rhenium catalyst.

In an embodiment, a suitable Raney nickel catalyst may be prepared by treating an alloy of approximately equal amounts by weight of nickel and aluminum with an aqueous alkali solution, e.g., containing about 25 weight % of sodium hydroxide. The aluminum is selectively dissolved by the aqueous alkali solution resulting in a sponge shaped material comprising mostly nickel with minor amounts of aluminum. The initial alloy includes promoter metals (e.g., molybdenum or chromium) in the amount such that 1 to 2 weight % remains in the formed sponge nickel catalyst. In another embodiment, the hydrogenation catalyst is prepared using a solution of ruthenium(III) nitrosylnitrate, ruthenium (III) chloride in water to impregnate a suitable support material. The solution is then dried to form a solid having a water content of less than 1% by weight. The solid is then reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the hydrogenation catalyst may include a catalyst support, which may be the same or different than a catalyst support used with the dehydrogenation and dimerization catalyst. In an embodiment, any of the catalyst supports discussed herein may be used to support a hydrogenation catalyst. The hydrogenation catalyst can be employed in any of the conventional types or structures known to the art. In an embodiment, any of the catalyst shapes and/or types discussed herein with respect to the dehydrogenation and dimerization catalyst may be used with the hydrogenation catalyst.

Production of Methyl Formate from Methanol

In addition to use of the systems and methods described herein for converting ethanol to ethyl acetate, those systems can also be used in processes with methanol as a feed instead of ethanol, with the production of methyl formate and $H_2$ as products according to the following formula:

$2CH_3OH \leftrightarrow HCOOCH_3 + 2H_2$

Such a system and method can utilize selections from the catalysts indicated for use with the ethanol feed. Products can be withdrawn in similar manner as described for the ethanol to ethyl acetate process.

EXAMPLES

The disclosure having been generally described, the following examples are given as particular embodiments of the disclosure and to demonstrate the practice and advantages thereof. It is understood that the examples are given by way of illustration and are not intended to limit the specification or the claims in any manner.

Example 1

Production of Ethyl Acetate from Ethanol

A 10 cm diameter distillation column is used, which has been rendered adiabatic by heating casings with temperatures controlled in such a way that the temperature gradient in the column is reproduced. Over a height of 3.5 m, the column is comprised of rectification zone with 8 stages each with a catalytic cell consisting of a cylindrical container with a flat bottom. The bottom of the container is equipped with a grid for retaining the catalyst and also can act as a gas and liquid distributor. The stripping zone is comprised of 12 stages, also with catalyst-containing cells. The rectification section is considered to be above the feed stage and the stripping section is considered to be below the feed stage. Each catalyst cell contains $CuO/ZnO/Al_2O_3$. 200 proof ethanol is fed to the 13$^{th}$ stage of the column, starting from the bottom.

The column is regulated by establishing a reflux ratio which is equal to 0.8, reboil ratio which is equal to 4 and controlling the base temperature to 211° C. and the absolute pressure to 20 bar. The reflux stream is mostly ethanol with small amounts of acetaldehyde. Under stabilized conditions, a bottoms stream and a distillate stream are collected with respective throughputs of about 170 g/h and 4 g/h. The bottoms product gives ethyl acetate purity of 98.5% with small amounts of n-butyraldehyde and butan-2-one.

Example 2

Selective Hydrogenation of n-butyraldehyde and butan-2-one

Selective hydrogenation of n-butyraldehyde and butan-2-one in the presence of ethyl acetate was conducted over a hydrogenation catalyst. The reactor was filled with 20 g of 0.1 wt % Pd on silica catalyst. Before the selective hydrogenation reaction, the catalyst was reduced at a temperature of 250° C. for 30 minutes. The catalyst reduction was conducted at atmospheric pressure by delivering hydrogen using a mass flow controller. At the end of this procedure, the catalyst was fully reduced.

The bottoms product from the reactive distillation column, whose composition is given in Table 2, was introduced to a heater at a rate of 30 g/h and mixed with hydrogen prior to admission to the selective hydrogenation reactor. The reaction product was cooled using a jacketed condenser and the liquid condensate was analyzed by gas chromatography. The results are summarized in Table 2, showing n-butyraldehyde and butan-2-one reduced to trace levels.

TABLE 2

| Hydrogenation Feed and Products | | |
|---|---|---|
| Temperature | 250° C. | |
| Pressure | 20 atm | |
| | Weight % | |
| Component | Feed | Products |
| Ethyl acetate | 93 | 92.9 |
| Ethanol | 2 | 2.1 |
| Iso-propanol | 3 | 3 |
| n-butyraldehyde | 1.5 | trace |
| butan-2-one | 0.5 | trace |
| 2-butanol | 0 | 0.48 |
| n-butanol | 0 | 1.52 |

Example 3

Wet-Impregnation Catalyst Preparation

Various catalysts including $CuO/SiO_2$, $CuO/SiO_2$—$Al_2O_3$, $CuO/ZnO$, $CuO/ZrO_2$, $CuO/SiO_2$—$ZrO_2$, $CuO/ZnO/Al_2O_3$, $CuO/Cr_2O_3/BaO$, $CuO/Cr_2O_3$ and $CuO/Al_2O_3$ were prepared via impregnation of the corresponding oxide catalyst support. The preparation involved dissolving 4 grams (g) of $Cu(NO_3)_2.2.5H_2O$ in 30 mL of de-ionized water, which was then added to 30 g of the appropriate oxide support and stirred until well mixed. The impregnated support was then dried in air at 110° C., followed by calcination in air at 450° C. The amount of $Cu(NO_3)_2.2.5H_2O$ was adjusted to achieve a desired final Cu weight loading. Enough water was used to wet the entire oxide support. Copper loadings between 0.5% and 20% by weight were achieved.

Example 4

Co-Impregnation and Sequential Impregnation Catalyst Preparation

Various catalysts including $CuO/ZnO/SiO_2$, $CuO/ZrO_2/SiO_2$, $CuO/MgO/SiO_2$, $CuO/CaO/SiO_2$, $CuO/SrO/SiO_2$, $CuO/BaO/SiO_2$, and $CuO/Na_2O/SiO_2$ were prepared via co-impregnation and sequential impregnation of a silica catalyst support. For the co-impregnation, measured amounts of $Cu(NO_3)_2.2.5H_2O$ and $M(NO_3)_x.YH_2O$ (M=Zn, Zr, Mg, Ca, Sr, Ca, or Na; X=1, 2, 4; Y=2-6) were dissolved in de-ionized water. The solution was added to the silica support and stirred until well mixed. The impregnated silica was dried in air at 110° C., followed by calcination in air at 450° C.

For the sequential impregnation, a measured amount of $M(NO_3)_x.YH_2O$ (M=Mg, Ca, Sr, Ca, or Na; X=1 or 2; Y=2-6) was dissolved in de-ionized water. The solution was then added to the silica support and mixed well. The silica was dried at 110° C. and then calcined at 450° C. in air. This procedure was then repeated using $Cu(NO_3)_2.2.5H_2O$ in place of the first metal nitrate. Copper loadings between 0.5% and 20% by weight and an addition metal loading between 0.1% and 10% by weight were achieved.

Example 5

Co-Precipitation Catalyst Preparation

Mixed-metal oxide catalysts were prepared via co-precipitation from nitrate solutions. In the co-precipitation synthesis, a measured amount of the appropriate metal nitrate (Cu, Zn, Zr, Al, Cr, Fe, Ni, and/or Ba) were dissolved in de-ionized water (total metal concentration ranges from 1-3 M). The metal-nitrate solution was then precipitated by drop-wise addition to a stirred, equal volume of 4 M aqueous NaOH at room temperature. After addition of all the metal nitrate solution, the suspension was stirred for an additional hour to ensure complete precipitation of the metals. The precipitated solid was then filtered and washed with excess de-ionized water. The solids were then dried overnight at 110° C. The resulting mixed metal oxide was then pressed, ground, and sieved to recover a catalyst with particle sizes between 450 and 850 μm. Catalysts prepared in this manner had copper oxide loadings between 40% and 80% by weight. The loadings of other metal oxides ranged from 2% to 40% by weight. In particular, $CuO/ZnO/ZrO_2/Al_2O_3$, and $CuO/ZnO/ZrO_2/Cr_2O_3$ catalysts were found to be especially active and selective for the dehydrogenative dimerization of ethanol, as illustrated below in Example 6.

In addition to the catalysts prepare above, various catalysts were prepared via co-precipitation and then a binder was incorporated. The catalyst binder was added to the mixed-metal oxide prepared as described above by first grinding the mixed-metal oxide to a fine powder and then stirring it into a colloidal suspension of silica or alumina in water. The resulting suspension was stirred while heating at 80-130° C. to dryness. The resulting solid was then be pressed, ground, and sieved to appropriate particle sizes.

Example 6

Dehydrogenative Dimerization of Ethanol

A portion of the catalysts prepared as described in Examples 3 to 5 were treated with a $Na_2CO_3$ solution by soaking the catalyst in a 0.2 M aqueous solution of $Na_2CO_3$ for 2-24 hrs. The catalyst was then filtered and allowed to dry in air at room temperature. Another portion of the catalysts prepared as described in Examples 3 to 5 were reduced in a hydrogen environment at 175-240° C. for a period of 4-12 hours. These catalysts were then tested in ethanol dehydrogenation reactions. Conversion and selectivity for gas phase reactions were determined from use in a fixed bed reactor operating at 190-240° C. and 1-24 atm. Pure ethanol was fed to the reactor with a weight hourly space velocity (WHSV) between 0.1-1.5 $hr^{-1}$. Conversion and selectivity for liquid phase and mixed liquid/vapor phase reactions were determined in a fixed bed reactor, operating at 190-240° C. and at pressures above 25 atm. Liquid phase reactions were also conducted in a batch reactor at 180-200° C. and 20-31 atm (the reactor pressure was maintained above the vapor pressure of ethanol at the operating temperature).

Table 3 shows the conversion and selectivity of the catalysts in a dehydrogenative dimerization reaction conducted in a fixed bed reactor. Conversion (X) and selectivity (S) were calculated from the composition of the reactor effluent as $$X_{ethanol} = 100 \left( \frac{F_{EtOH,0} - F_{EtOH}}{F_{EtOH,0}} \right)$$

$$S = 100 \left( \frac{2F_{EtOAC} + F_{AcH}}{F_{EtOH,0} - F_{EtOH}} \right)$$

where $F_{EtOH}$, $F_{EtOAc}$, and $F_{AcH}$ represent the molar flow rates of ethanol, ethyl acetate, and acetaldehyde in the reactor effluent, respectively, and $F_{EtOH,0}$ represents the molar flow rate of ethanol into the reactor inlet. Acetaldehyde is a reaction intermediate and so was included in the selectivity calculation.

TABLE 3

Conversion and Selectivity for selected catalysts in a fixed bed reactor at 220° C. and 1 atm

| Catalyst sample | As prepared/received | | Reduced in $H_2$ | |
|---|---|---|---|---|
| | X | S | X | S |
| Pellet catalysts | | | | |
| $CuO/ZnO/Al_2O_3$ | 18.9 | 92.4 | 35.0 | 89.7 |
| $CuO/Cr_2O_3/BaO$ | 43.5 | 89.4 | 36.0 | 74.6 |
| Impregnated catalysts | | | | |
| $CuO/SiO_2$ | 19.6 | 96.2 | 22.5 | 80.9 |
| $CuO/SiO_2$—$Al_2O_3$ | 43.0 | 17.0 | | |
| $CuO/Al_2O_3$ | 50.2 | 47.3 | | |
| $CuO/ZnO$ | 19.7 | 65.5 | | |
| $CuO/ZrO_2$ | 41.5 | 63.4 | | |
| $CuO/SiO_2$—$ZrO_2$ | 40.0 | 59.7 | | |
| $CuO/MgO/SiO_2$ | 37.9 | 70.0 | 32.1 | 65.7 |
| $CuO/CaO/SiO_2$ | 33.3 | 73.4 | 29.0 | 42.7 |
| $CuO/SrO/SiO_2$ | 25.1 | 77.2 | 31.5 | 69.6 |
| $CuO/BaO/SiO_2$ | 31.0 | 73.2 | 33.6 | 73.6 |
| $CuO/Na_2O/SiO_2$ | 19.4 | 95.9 | | |
| $CuO/ZrO_2/SiO_2$ | 39.1 | 58.7 | 54.0 | 61.6 |
| Co-precipitation catalysts | | | | |
| $CuO/ZnO/ZrO_2/Al_2O_3$ | 8.7 | 83.6 | 21.4 | 72.6 |
| $CuO/ZnO/ZrO_2/Al_2O_3/Na_2CO_3$ | 26.1 | 40.1 | 39.0 | 86.1 |
| $CuO/ZnO/ZrO_2/Cr_2O_3$ | 28.8 | 92.0 | 20.9 | 80.9 |
| $CuO/ZnO/ZrO_2/Cr_2O_3/Na_2CO_3$ | 37.0 | 90.2 | 35.9 | 87.5 |
| $CuO/ZnO/ZrO_2/Fe_2O_3$ | 34.1 | 92.1 | 17.0 | 94.2 |
| $CuO/ZnO/ZrO_2/Fe_2O_3/Na_2CO_3$ | 30.7 | 72.6 | | |
| $CuO/ZnO/ZrO_2/Al_2O_3/Cr_2O_3$ | 24.5 | 88.4 | 18.5 | 79.4 |
| $CuO/ZnO/ZrO_2/Al_2O_3/Cr_2O_3/Na_2CO_3$ | 33.2 | 86.3 | | |

Example 7

Pressure Effects on the Conversion

A fixed bed reactor operated under similar conditions to those described with respect to Example 6 was used to test the reaction conversion and selectivity of a catalyst under varying reaction pressures. Table 4 shows a typical trend in the conversion and selectivity of these catalysts when operated at elevated pressures. Similar trends were seen for all catalysts tested at elevated pressures.

TABLE 4

Conversion and Selectivity for $CuO/ZnO/ZrO_2/Al_2O_3/Na_2CO_3$ (reduced at 240° C. in $H_2$) in a fixed bed reactor at 220° C.

| Pressure (atm) | X | S |
|---|---|---|
| 1 | 39.0 | 86.1 |
| 9.4 | 43.6 | 96.1 |
| 14.5 | 43.3 | 96.4 |
| 21.4 | 39.3 | 97.4 |

As seen by the results in Table 4, operation of catalysts at higher pressures increases the selectivity of the catalyst significantly. Increasing the pressure had little effect on the conversion achieved by the catalysts.

Example 8

Liquid Phase Reaction

The dehydrogenative dimerization of ethanol was also conducted in the liquid phase. Reaction temperatures ranged from 180 to 200° C. and pressures were kept above the vapor pressure of ethanol at the reaction temperature (25-36 atm). Liquid phase reactions were conducted in both a fixed bed reactor and batch reactor. Table 5 shows the results for a CuO/ZnO/Al2O3 catalyst in a batch reactor operating in the liquid phase. During a typical batch reaction, the pressure initially reached the vapor pressure of ethanol and then slowly increased beyond that pressure as the reaction generated $H_2$ gas. The batch reactor results demonstrated that the dehydrogenative dimerization reaction occurs in the liquid phase.

TABLE 5

Conversion and Selectivity for CuO/ZnO/Al$_2$O$_3$ (reduced at 240° C. in H$_2$) after 2 hrs in a batch reactor.

| Temperature (° C.) | X | S |
|---|---|---|
| 180 | 4.4 | 84.1 |
| 190 | 6.1 | 81.5 |
| 200 | 13.0 | 96.1 |

Based on the results of Examples 3 through 8, it can be seen that a high selectivity to ethyl acetate using the dehydrogenation and dimerization catalysts described herein (e.g., CuO/ZnO/ZrO$_2$/Al$_2$O$_3$/Na$_2$CO$_3$ and/or CuO/ZnO/Al$_2$O$_3$) should enable the use of the system embodiments as illustrated in FIGS. 3, 5 and 7 of the present disclosure. For catalysts where 2-butanone is produced above acceptable levels, the use of the system embodiments as illustrated in FIGS. 4, 6 and 8 of the present disclosure may be used.

Example 9

Effect of Water in the Ethanol Feed

In this example, the effect of water in the ethanol feed was investigated. A 4 wt % water in ethanol solution was fed to a CuO/ZnO/Al$_2$O$_3$ catalyst in a fixed bed reactor to demonstrate the water tolerance of the catalyst. The reactor was maintained at 21.4 atm and the catalyst was heated to 200-240° C. Table 6 compares the conversion and selectivity achieved for both the 4 wt % water in ethanol and a pure ethanol feed.

TABLE 6

Conversion and selectivity for CuO/ZnO/Al$_2$O$_3$ in a fixed bed reactor operating at 21.4 atm for ethanol feeds with and without water.

| Temperature | Pure Ethanol Feed | | 4% Water in Ethanol Feed | |
|---|---|---|---|---|
| (° C.) | Conversion | Selectivity | Conversion | Selectivity |
| 200 | 23.2 | 98.1 | 14.2 | 99.2 |
| 220 | 37.9 | 97.1 | 29.2 | 98.6 |
| 240 | 47.9 | 94.4 | 42.6 | 98.0 |

Example 10

Impregnated Catalysts

A catalyst comprising CuO/ZrO$_2$/Al$_2$O$_3$ was prepared via co-impregnation of an alumina support. As in a typical co-impregnation, measured amounts of Cu(NO$_3$)$_2$.2.5H$_2$O and ZrO(NO$_3$)$_2$.6H$_2$O were dissolved in an appropriate amount of de-ionized water to fill the pore volume of the alumina support. The solution was added to the alumina support and agitated until the liquid was fully absorbed by the alumina. The impregnated alumina was dried in air at 110° C., followed by calcination in air at 400-600° C. for 2-10 hours. Typical catalyst loadings ranged from 1-50 wt % CuO and 2-40 wt % ZrO$_2$, and some of the catalyst weight loadings were about 13 wt % CuO and about 7 wt % ZrO$_2$.

The supported CuO/ZrO$_2$/Al$_2$O$_3$ could be treated with a base such as sodium carbonate after the calcination to improve catalyst selectivity. For these catalysts, a volume of an aqueous sodium carbonate solution sufficient to fully submerge the supported catalyst was prepared (0.1-1.0 M). The catalyst was then added to the solution and allowed to cure for 2-12 hours at room temperature. The catalyst was then filtered and washed to remove the excess base, then dried prior to use in a reaction. Bases other than sodium carbonate that could be used include K$_2$CO$_3$, Li$_2$CO$_3$, Cs$_2$CO$_3$, NaOH, Ca(OH)$_2$, KOH, CsOH, Ba(OH)$_2$.

The results of the impregnated catalyst are shown below in Table 7, wherein X and S are based on the formulas provided above in Example 6.

TABLE 7

Conversion and Selectivity for selected supported catalysts in a fixed bed reactor operating at 200° C. and 33 atm with an LHSV = 0.5 hr$^{-1}$.

| Catalyst sample | As prepared | |
|---|---|---|
| Impregnated catalyst | X | S |
| CuO/ZrO$_2$ on Al$_2$O$_3$ | 13.8 | 95.1 |

Example 11

Co-Precipitation Catalyst Preparation

Mixed-metal oxide catalysts comprising CuO/ZrO$_2$/Al$_2$O$_3$ and CuO/ZrO$_2$ were prepared via co-precipitation from nitrate solutions. As in a typical co-precipitation synthesis, a measured amount of the appropriate metal nitrates were dissolved in de-ionized water (total metal concentration ranges from 0.5-3 M). The metal-nitrate solution was then precipitated by drop-wise addition into a stirred, equal volume of 1-4 M aqueous NaOH. The NaOH solution could be at room temperature or heated up to near boiling. After addition of all the metal nitrate solution, the suspension was stirred for 2-24 hours to ensure complete precipitation of the metal oxides. The precipitated solid was then filtered and washed with excess de-ionized water. The solids were then dried at 110° C., followed by calcination at 220-500° C. Catalysts prepared in this manner had CuO loadings between about 40 to about 80 wt %. The loadings of other metal oxides range from about 2 to about 40 wt %. Other metal salts, such as acetates and carbonates, could be used in place of the nitrates.

A catalyst binder could be added to the mixed-metal oxide to impart additional mechanical strength. The metal oxide catalyst would be ground to a fine powder and then stirred into a suspension of the binder. The resulting slurry could then be extruded or pressed, ground, and sieved to appropriate particle sizes. An alternative could include adding the binder material to the NaOH precipitation solution prior to addition of the metal nitrate solution. Binders can include $SiO_2$, $Al_2O_3$, bentonite and other clays, hydrotalcite, and $Al(OH)_3$.

The results of the co-precipitation catalyst are shown below in Table 8, wherein X and S are based on the formulas provided above in Example 6.

TABLE 8

Conversion and Selectivity for selected supported catalysts in a fixed bed reactor operating at 200° C. and 33 atm with an LHSV = 0.5 $hr^{-1}$.

| Catalyst sample | As prepared | |
|---|---|---|
| Co-Precipitation Catalyst | X | S |
| $CuO/ZrO_2$ | 17.2 | 96.2 |
| $Cu/O/ZrO_2/Al_2O_3$ | 17.8 | 98.6 |

Example 12

Figure 16:
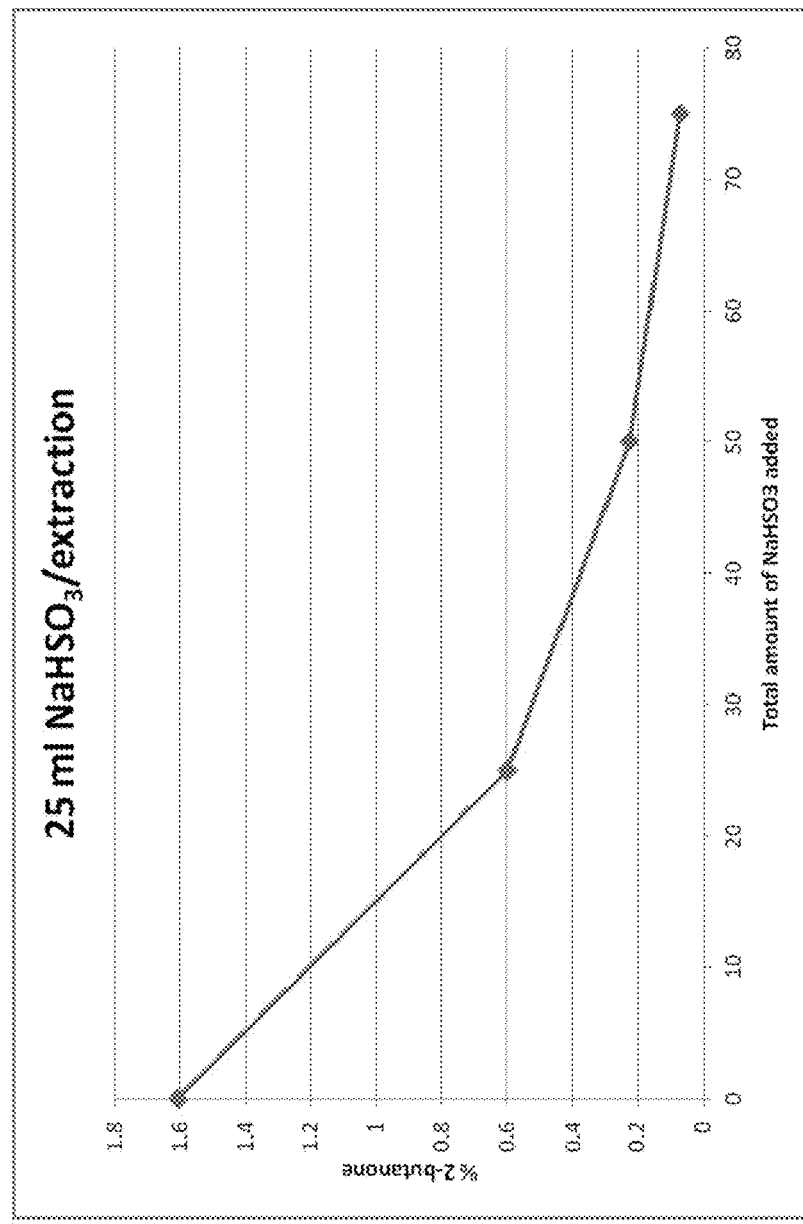
FIG. 16 illustrates a chart demonstrating the results of an extraction of 2-butanone from ethyl acetate.

In order to demonstrate the extraction of impurities from ethyl acetate using an aqueous solution comprising an extracting agent, a solution of sodium hydrogen sulfite ($NaHSO_3$) was prepare using 30 grams of sodium hydrogen sulfite per 100 milliliters of water. A product stream was simulated by preparing an ethyl acetate solution containing 1.6 wt. % 2-butanone. The extraction was first conducted by sequentially contact 100 milliliters of the ethyl acetate with 25 milliliters of the aqueous solution at a time. For each extraction, the ethyl acetate solution was mixed with the 25 milliliters of the aqueous $NaHSO_3$ solution. The separation funnel was vigorously shaken several times at room temperature then allowed to rest and let the ethyl acetate-water phase separation take place. The heavier, aqueous phase was drained and replaced with same amount of fresh $NaHSO_3$ solution, and the procedure was repeated as needed until the 2-butanone level drops below the desired level. The residual concentration of the 2-butanone was tracked with a GC analysis after each extraction step. The results of the analysis are illustrated in FIG. 16.

The results demonstrate that 3 consecutive washes resulted in a final 2-butanone concentration below 0.1 wt. %. Similar behavior would be expected for other ketones and aldehydes such as acetone and acetaldehyde.

Example 13

Figure 17:
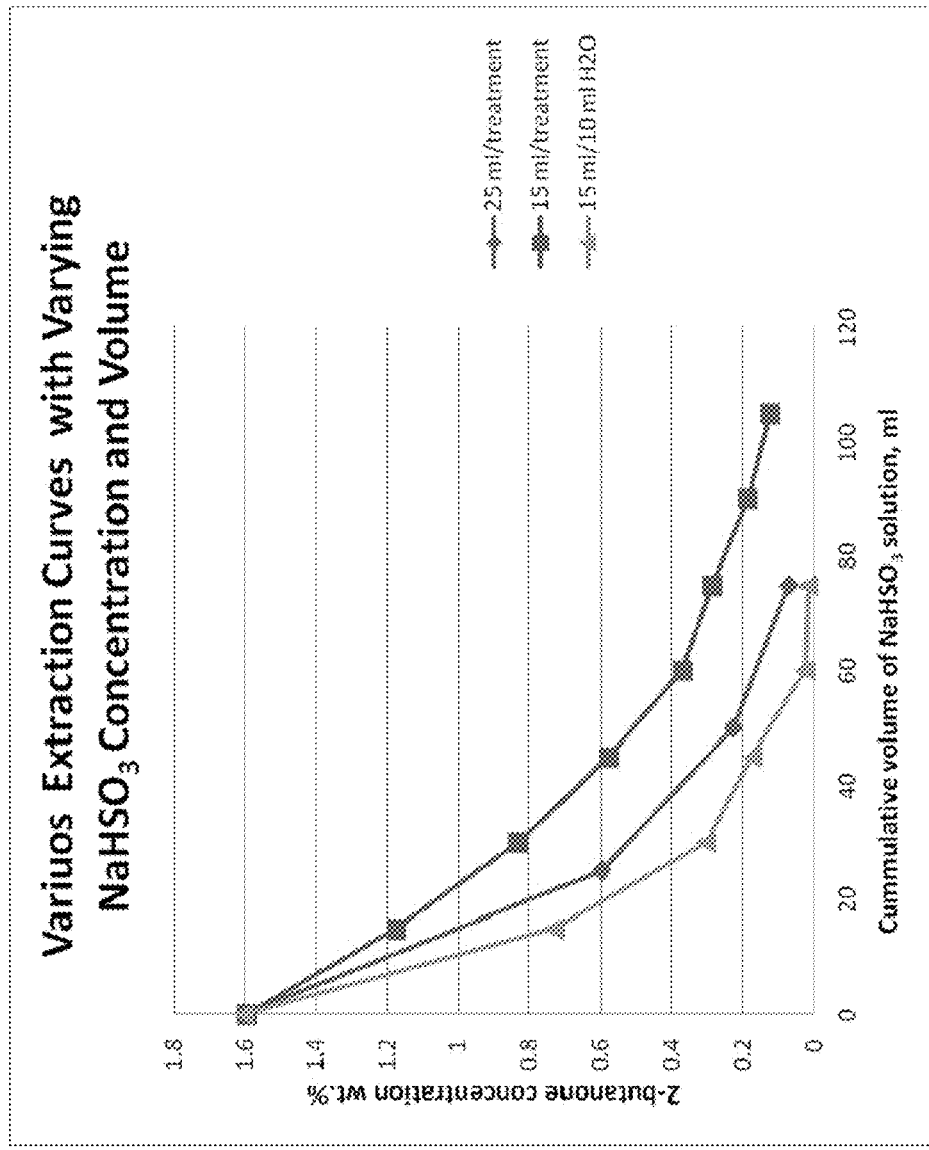
FIG. 17 illustrates another chart demonstrating the results of an extraction of 2-butanone from ethyl acetate.

The effect of the extraction efficiency with respect to the volume and concentration of the solvent was explored in this example. In this example, the effects on the 2-butanone concentration in the ethyl acetate solution were determined using different volumes of solvent as well as different concentrations of the extracting agent in the solvent. The same ethyl acetate solution comprising 1.6 wt. % 2-butanone was prepared as in Example 12. The starting solvent solution included 30 grams of sodium hydrogen sulfite per 100 milliliters of water. A volume of 75 milliliters of the ethyl acetate solution was first contacted with 25 milliliters of the solvent solution in multiple extraction steps that were carried out as described above in Example 12. The concentration of the 2-butanone was measured after each step and the results are shown in FIG. 17. Another volume of 75 milliliters of the ethyl acetate solution was then contacted with 15 milliliters of the solvent solution in multiple extraction steps. A fresh volume of 75 milliliters of the ethyl acetate solution was then contacted in multiple extraction steps with 25 milliliters of the solvent solution that was prepared by diluting 15 milliliters of the original solvent solution (30 grams of sodium hydrogen sulfite per 100 milliliters of water) with 10 milliliters of water. The concentration of the 2-butanone was measured after each step and the results are shown in FIG. 17.

The results indicate that smaller volumes with the same concentration of $NaHSO_3$ (15 ml extraction volumes) is less efficient than larger ones (25 ml as shown in FIG. 16). Furthermore, a dilution of the $NaHSO_3$ solution yielded improved removal efficiency and reduced tendency to form crystals (FIG. 17). This unexpected results is likely due to the higher solubility of the sodium sulfite 2-butanone adduct in a less concentrated aqueous $NaHSO_3$ salt solution. Thus we discovered that optimal removal rates are not achieved by excessively high concentrations of $NaHSO_3$ or small extraction volumes but with concentration that is high enough to provide $NaHSO_3$ excess but not suppress the removal of the sodium sulfite 2-butanone adduct which has to dissolve in the aqueous phase.

Example 14

The effect of the extraction temperature explored in this example. In this example, an identical amount of ethyl acetate was treated with the same amount and the same concentration of the aqueous $NaHSO_3$ (30 grams of sodium hydrogen sulfite per 100 milliliters of water). The first sample was kept cooled for 2 hours at approximately 4° C. The final concentration of the 2-butanone in the sample maintained at 4° C. was measured by a gas chromatograph analysis as 0.08 wt. %. The sample maintained at room temperature (approximately 25° C.) had a final concentration of about 0.18%. Thus, a greater amount of the 2-butanone was transferred from the ethyl acetate sample into the solvent solution in the sample maintained at 4° C. than the sample maintained at room temperature.

Example 15

The effect of the use of mixtures of sodium sulfite and sodium hydrogen sulfite was explored in this example. The sodium sulfite solution ($Na_2SO_3$) was prepared in situ by the addition of NaOH to a solution of $NaHSO_3$. A stoichiometric amount of NaOH can be used to completely convert an amount of $NaHSO_3$ into $Na_2SO_3$. A less than stoichiometric amount of NaOH can be used to create a mixture of $Na_2SO_3$ and $NaHSO_3$. Tests were performed with a solution of $NaHSO_3$ that was neutralized with NaOH to a 50% solution (corresponding to a mixture of 50% $NaHSO_3$ and 50% $Na_2SO_3$) as well as a solution of $NaHSO_3$ that was neutralized with NaOH to a 100% solution (corresponding to substantially pure aqueous $Na_2SO_3$). Several multi-step extractions were performed on a solution comprising ethyl acetate solution comprising 1.86 wt. % 2-butanone. The results are presented in FIG. 18.

Figure 18:
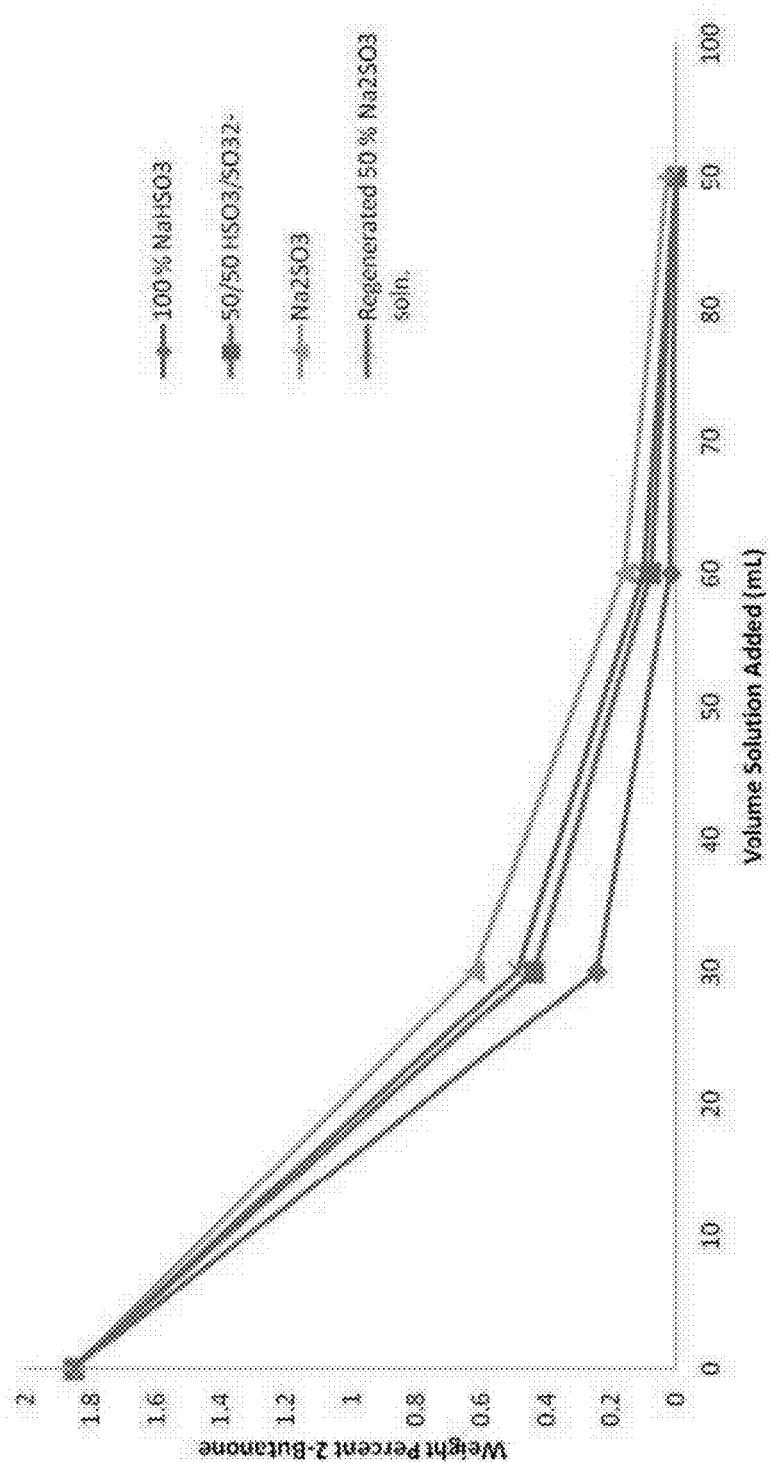
FIG. 18 illustrates another chart demonstrating the results of an extraction of 2-butanone from ethyl acetate using several extracting solution compositions.

As shown in FIG. 18, each point on the graph represents an extraction, wherein the x-axis represents the cumulative amount of extractant solution used. The starting solution of $NaHSO_3$ contained approximately 30 grams of $NaHSO_3/100$ ml. The exact concentration was determined by iodometric titration and the solution was adjusted with 4 M NaOH as needed to achieve the desired neutralization level. Although the tests demonstrate that the performance of the $Na_2SO_3$ containing extraction was slightly lower, the regeneration of $Na_2SO_3$ solution is expected to be much more reproducible and with lower potential release of $SO_2$ gas. A similar performance is expected from corresponding mixtures of $NaHSO_3$ and $Na_2SO_3$.

Additional Embodiments

Having described the systems and methods, various embodiments may include, but are not limited to:

In a first embodiment, a method of purifying an ethyl acetate stream comprises contacting an inlet stream with a solvent, transferring at least a portion of the impurity compound from the inlet stream into the solvent to form an extract and a purified product, separating the extract from the purified product, separating the portion of the impurity compound from the extract, forming an impurities stream and a regenerated solvent, and recycling at least a portion of the regenerated solvent to contact the inlet stream. The inlet stream comprises ethyl acetate and an impurity compound, and the extract comprises the solvent and the portion of the impurity compound transferred from the inlet stream. In a second embodiment, the solvent of the first embodiment may comprise an aqueous fluid. In a third embodiment, the method of the first or second embodiment can also include heating the extract after separating the extract from the purified product. Heating the extract can include heating the extract to a temperature between about 85 45° C. and about 100° C. In a fourth embodiment, the solvent of any of the first to third embodiments can also include an extracting agent, and the extracting agent may be configured to increase the solubility of the impurity compound in the solvent. In a fifth embodiment, the extracting agent of the fourth embodiment may comprise sodium hydrogen sulfite. In a sixth embodiment, the extracting agent of the fourth embodiment may comprise a compound selected from the group consisting of: hydrosulfite ion, sulfite ion, hydrazine, hydroxylamine, semicarbazide, phenylhydrazine, phenylhydroxylamine, salts thereof, aqueous solutions thereof, and any combination thereof. In a seventh embodiment, the method of any of the fourth to sixth embodiments can also include reacting the extracting agent and the impurity compound to form an adduct in response to contacting the inlet stream with the solvent. In an eighth embodiment, separating the portion of the impurity compound from the extract in the seventh embodiment may comprise dissociating the adduct. In a ninth embodiment, the impurity compound of any of the first to eighth embodiments may comprise at least one of a ketone, an aldehyde, or any combination thereof. In a tenth embodiment, the method of any of the first to ninth embodiments may comprise drying the purified product. In an eleventh embodiment, the purified product of any of the first to tenth embodiments may comprise at least about 90% ethyl acetate by weight. In a twelfth embodiment, contacting the inlet stream with the solvent in any of the first to eleventh embodiments may comprise at least one of contacting the inlet stream with the solvent in a counter-current flow, or contacting the inlet stream with the solvent in a cross-current flow. In a thirteenth embodiment, the method of any of the first to twelfth embodiments can also include feeding a feed stream comprising ethanol to a reactive distillation column, contacting the ethanol with a catalyst, dehydrogenating ethanol over the catalyst, removing ethyl acetate during the distillation process as a liquid bottoms product, removing hydrogen during the distillation process as a gaseous top product, and providing the ethyl acetate as the inlet stream. In a fourteenth embodiment, the catalyst of the thirteenth embodiment may be disposed in a side reactor, and the side reactor may be in fluid communication with the reactive distillation column. In a fifteenth embodiment, the catalyst of the fourteenth embodiment may be disposed in the reactive distillation column. In a sixteenth embodiment, separating the portion of the impurity compound from the extract in any of the first to fifteenth embodiments may comprise contacting the extract with a purge gas, transferring at least a portion of the impurity compound from the extract to the purge gas, and separating the purge gas from at least the portion of the impurity compound. In a seventeenth embodiment, separating the portion of the impurity compound from the extract in any of the first to sixteenth embodiments may occur at a pressure of between about 0.001 atm and about 1 atm.

In an eighteenth embodiment, a reactive distillation system for producing high purity ethyl acetate from ethanol comprises a reactive distillation column, an extraction unit, and a stripping unit. The reactive distillation column comprises a dehydrogenation catalyst, an ethanol inlet configured to pass an ethanol feed over the dehydrogenation catalyst, a top product gaseous hydrogen removal passage, and a bottoms product liquid ethyl acetate removal passage. The extraction unit is configured to receive a liquid ethyl acetate product stream from the reactive distillation column through the bottoms product liquid ethyl acetate removal passage, contact a liquid solvent feed stream with the liquid ethyl acetate product stream, provide an extract stream comprising a portion of any impurities in the liquid ethyl acetate product stream, and provide a purified product stream. The stripping unit is configured to receive the extract stream from the extraction unit, separate the portion of the impurities from the extract stream, provide an outlet impurities stream, and provide a regenerated solvent stream back to the extraction unit as at least a portion of the liquid solvent feed stream. In a nineteenth embodiment, the system of the eighteenth embodiment can also include a drying unit, and the drying unit can be configured to receive the purified product stream from the extraction unit, remove at least a portion of any water in the purified product stream, and provide a dried purified product stream. In a twentieth embodiment, the extraction unit of the eighteenth or nineteenth embodiments may be configured to contact the liquid solvent feed stream with the liquid ethyl acetate product stream using a counter-current flow. In a twenty first embodiment, the extraction unit of the eighteenth or nineteenth embodiments may be configured to contact the liquid solvent feed stream with the liquid ethyl acetate product stream using a cross-current flow. In a twenty second embodiment, the extraction unit of any of the eighteenth to twenty first embodiments may comprise a liquid-liquid contact vessel. In a twenty third embodiment, the liquid-liquid contact vessel of the twenty second embodiment may comprise packing. In a twenty fourth embodiment, the stripping unit of any of the eighteenth to twenty third embodiments may comprise a distillation column. In a twenty fifth embodiment, the distillation column of the twenty fourth embodiment may comprise between about 1 and about 50 stages. In a twenty sixth embodiment, the system of any of the eighteenth to twenty fifth embodiments can also include a cooler, and the cooler can be configured to receive the regenerated solvent stream, cool the regenerated solvent stream, and provide the cooled regenerated solvent stream back to the extraction unit. In a twenty seventh embodiment, the system of any of the eighteenth to twenty sixth embodiments may also include at least one side reactor in fluid communication with the reactive distillation column. In a twenty eighth embodiment, the system of the twenty seventh embodiment may also include a second catalyst disposed in the at least one side reactor, wherein the catalyst comprises at least one of a dehydrogenation catalyst or a hydrogenation catalyst.

In a twenty ninth embodiment, a reactive distillation process producing high purity ethyl acetate from ethanol comprises feeding a feed stream comprising ethanol to a reactive distillation column, contacting the ethanol with a catalyst, dehydrogenating ethanol over the catalyst in the liquid phase during the distillation process, removing ethyl acetate during the distillation process as a bottoms product, and removing hydrogen during the distillation process as a top product. In a thirtieth embodiment, the reactive distillation process of the twenty ninth embodiment may also include contacting the bottoms stream with a hydrogenation catalyst and hydrogen, hydrogenating at least a portion of a contaminant in the bottoms stream, and separating the hydrogenated portion of the contaminant from the bottoms stream. In a thirty first embodiment, separating the hydrogenated portion of the contaminant from the bottoms stream in the thirtieth embodiment comprises distilling the hydrogenated portion of the contaminant from the bottoms stream. In a thirty second embodiment, the contacting, the hydrogenating, and the separating in the thirtieth or thirty first embodiments may occur downstream of the reactive distillation column. In a thirty third embodiment, the contaminant of any of the thirtieth to thirty second embodiments may comprise a ketone or an aldehyde. In a thirty fourth embodiment, the reactive distillation process of any of the twenty ninth to thirty third embodiments may also include extracting at least a portion of a contaminant in the bottoms stream using a solvent to produce an extract stream and a purified product stream, and stripping the portion of the contaminant from the extract stream to produce a contaminant stream and regenerate the solvent stream. In a thirty fifth embodiment, the reactive distillation process of any of the twenty ninth to thirty fourth embodiments may also include contacting a first fluid drawn from the reactive distillation column with the catalyst in a side reactor, and introducing the second fluid to the reactive distillation column during the distillation process. The first fluid may react in the presence of the catalyst to produce a reaction product comprising a second fluid. In a thirty sixth embodiment, the reactive distillation process of the thirty fifth embodiment may also include increasing a contact time between the ethanol and the catalyst, and improving a conversion of ethanol to ethyl acetate in response to increasing the contact time between the ethanol and the catalyst. In a thirty seventh embodiment, the reactive distillation process of the thirty fifth to thirty sixth embodiments may also include contacting the bottoms stream with a hydrogenation catalyst and hydrogen, hydrogenating at least a portion of a contaminant in the bottoms stream, and separating the hydrogenated portion of the contaminant from the bottoms stream. In a thirty eighth embodiment, the bottoms product of any of the twenty ninth to thirty seventh embodiments may comprise at least about 90% ethyl acetate. In a thirty ninth embodiment, the feed stream comprising ethanol of any of the twenty ninth to thirty eighth embodiments may be the only feed stream fed to the reactive distillation column. In a fortieth embodiment, the catalyst of any of the twenty ninth to thirty ninth embodiments may be disposed within the reactive distillation column. In a forty first embodiment, the reactive distillation process of any of the twenty ninth to fortieth embodiments may also include introducing a second feed stream to the reactive distillation column, and contacting the second feed stream with a hydrogenation catalyst during the distillation process. The second feed stream may comprise hydrogen.

In the preceding discussion and in the claims, the terms "including" and "comprising" are used in an open-ended fashion, and thus should be interpreted to mean "including, but not limited to . . . ". At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present invention.

What is claimed is:

1. A method of purifying an ethyl acetate stream comprising:
    contacting an inlet stream with a solvent, wherein the inlet stream comprises ethyl acetate and an impurity compound, wherein the impurity compound comprises at least one of a ketone, an aldehyde, or any combination thereof, wherein the impurity compound comprises 2-butanone;
    transferring at least a portion of the impurity compound from the inlet stream into the solvent to form an extract and a purified product, wherein the extract comprises the solvent and the portion of the impurity compound transferred from the inlet stream;
    separating the extract from the purified product;
    separating the portion of the impurity compound from the extract;
    forming an impurities stream and a regenerated solvent; and
    recycling at least a portion of the regenerated solvent to contact the inlet stream.

2. The method of claim 1, wherein the solvent comprises an aqueous fluid.

3. The method of claim 1, wherein the solvent further comprises an extracting agent, wherein the impurity compound has a higher solubility in the solvent comprising the extracting agent than in the solvent without the extracting agent.

4. The method of claim 3, wherein the extracting agent comprises sodium hydrogen sulfite.

5. The method of claim 3, wherein the extracting agent comprises a compound selected from the group consisting of: hydrosulfite ion, sulfite ion, hydrazine, hydroxylamine, semicarbazide, phenylhydrazine, phenylhydroxylamine, salts thereof, aqueous solutions thereof, and any combination thereof.

6. The method of claim 3, further comprising reacting the extracting agent and the impurity compound to form an adduct in response to contacting the inlet stream with the solvent.

7. The method of claim 6, wherein separating the portion of the impurity compound from the extract comprises dissociating the adduct.

8. The method of claim 1, wherein the purified product comprises at least about 90% ethyl acetate by weight.

9. The method of claim 1, wherein contacting the inlet stream with the solvent comprises at least one of contacting the inlet stream with the solvent in a counter-current flow, or contacting the inlet stream with the solvent in a cross-current flow.

10. The method of claim 1, further comprising:
feeding a feed stream comprising ethanol to a reactive distillation column;
contacting the ethanol with a catalyst;
dehydrogenating ethanol over the catalyst;
removing ethyl acetate during the distillation process as a liquid bottoms product;
removing hydrogen during the distillation process as a gaseous top product; and
providing at least a portion of the ethyl acetate as the inlet stream.

11. The method of claim 10, wherein the catalyst is disposed in a side reactor, and wherein the side reactor is in fluid communication with the reactive distillation column.

12. The method of claim 1, wherein separating the portion of the impurity compound from the extract comprises: contacting the extract with a purge gas, transferring at least a portion of the impurity compound from the extract to the purge gas, and separating the purge gas from at least the portion of the impurity compound.

13. The method of claim 1, wherein separating the portion of the impurity compound from the extract occurs at a pressure of between about 0.001 atm and about 1 atm.

14. The method of claim 10, wherein dehydrogenating ethanol over the catalyst occurs in the liquid phase during the distillation process.

15. The method of claim 14, further comprising:
contacting the liquid bottoms product with a hydrogenation catalyst and hydrogen;
hydrogenating at least a portion of a contaminant in the liquid bottoms product, wherein the contaminant comprises the impurity compound; and
separating the hydrogenated portion of the contaminant from the liquid bottoms product.

16. The method of claim 15, wherein the contacting of the liquid bottoms product with the hydrogenation catalyst and hydrogen, the hydrogenating, and the separating of the hydrogenated portion of the contaminant occur downstream of the reactive distillation column.

17. The reactive distillation process of claim 10, further comprising:
contacting a first fluid drawn from the reactive distillation column with the catalyst in a side reactor, wherein the first fluid reacts in the presence of the catalyst to produce a reaction product comprising a second fluid; and
introducing the second fluid to the reactive distillation column during the distillation process.

18. The reactive distillation process of claim 17, further comprising:
increasing the contact time between the ethanol and the catalyst; and
improving the conversion of ethanol to ethyl acetate in response to increasing the contact time between the ethanol and the catalyst.

19. The reactive distillation process of claim 17, further comprising:
contacting the liquid bottoms product with a hydrogenation catalyst and hydrogen;
hydrogenating at least a portion of a contaminant in the liquid bottoms product; and
separating the hydrogenated portion of the contaminant from the liquid bottoms product.

20. The reactive distillation process of claim 14, wherein the liquid bottoms product comprises at least about 90% ethyl acetate.

21. The method of claim 1, further comprising: removing at least a portion of any water in the purified product stream to form a dried purified product stream.

22. The method of claim 1, wherein transferring at least the portion of the impurity product from the inlet stream into the solvent occurs in an extraction unit, and wherein the extraction unit comprises a liquid-liquid contact vessel.

23. The method of claim 1, wherein separating the portion of the impurity product from the extract occurs in a stripping unit, and wherein the stripping unit comprises a distillation column.

24. A method of purifying an organic stream comprising:
contacting a liquid inlet stream with an aqueous solvent, wherein the inlet stream comprises: an ester comprising ethyl acetate, and an impurity compound comprising at least one of a ketone, an aldehyde, or a combination thereof, wherein the impurity compound comprises 2-butanone;
transferring at least a portion of the impurity compound from the inlet stream into the solvent to form an extract and a purified product, wherein the extract comprises the solvent and the portion of the impurity compound transferred from the inlet stream;
separating the extract from the purified product;
separating the portion of the impurity compound from the extract;
forming an impurities stream and a regenerated solvent; and
recycling at least a portion of the regenerated solvent to contact the inlet stream.

25. The method of claim 24, wherein a majority of the ethyl acetate in the liquid inlet stream is separated into the purified product.

26. The method of claim 24, wherein the solvent comprises an extracting agent, and wherein the extracting agent comprises a compound selected from the group consisting of: hydrosulfite ion, sulfite ion, hydrazine, hydroxylamine, semicarbazide, phenylhydrazine, phenylhydroxylamine, salts thereof, aqueous solutions thereof, and any combination thereof.

* * * * *